(12) United States Patent
Elings et al.

(10) Patent No.: US 9,594,029 B2
(45) Date of Patent: Mar. 14, 2017

(54) METHODS AND APPARATUS FOR MEASURING A PROPERTY OF A SUBSTRATE

(71) Applicant: ASML Netherlands B.V., Veldhoven (NL)

(72) Inventors: Wouter Lodewijk Elings, Taipei (TW); Franciscus Bernardus Maria Van Bilsen, Eindhoven (NL); Christianus Gerardus Maria De Mol, Son en Breugel (NL); Everhardus Cornelis Mos, Best (NL); Hoite Pieter Theodoor Tolsma, Eindhoven (NL); Peter Ten Berge, Eindhoven (NL); Paul Jacques Van Wijnen, Veldhoven (NL); Leonardus Henricus Marie Verstappen, Weert (NL); Gerald Dicker, Taipei (TW); Reiner Maria Jungblut, Taipei (TW); Li Chung-Hsun, Eindhoven (NL)

(73) Assignee: ASML Netherlands B.V., Veldhoven (NL)

(*) Notice: Subject to any disclaimer, the term of this patent is extended or adjusted under 35 U.S.C. 154(b) by 287 days.

(21) Appl. No.: 14/355,962

(22) PCT Filed: Nov. 22, 2012

(86) PCT No.: PCT/EP2012/073396
§ 371 (c)(1),
(2) Date: May 2, 2014

(87) PCT Pub. No.: WO2013/092106
PCT Pub. Date: Jun. 27, 2013

(65) Prior Publication Data
US 2014/0354969 A1    Dec. 4, 2014

Related U.S. Application Data

(60) Provisional application No. 61/579,969, filed on Dec. 23, 2011.

(51) Int. Cl.
*G01N 21/95* (2006.01)
*G01B 11/02* (2006.01)
(Continued)

(52) U.S. Cl.
CPC ......... *G01N 21/9501* (2013.01); *G01B 11/02* (2013.01); *G01B 11/14* (2013.01);
(Continued)

(58) Field of Classification Search
CPC ........ G01B 11/02; G01B 11/14; G01N 21/47; G01N 21/4788; G01N 21/9501;
(Continued)

(56) References Cited

U.S. PATENT DOCUMENTS 5,982,920 A * 11/1999 Tobin, Jr. .............. G06T 7/0004
382/145
6,233,494 B1    5/2001 Aoyagi
(Continued)

FOREIGN PATENT DOCUMENTS

EP         1 628 164 A2    2/2006
WO    WO 2011/045125 A1    4/2011
WO    WO 2011/151121 A1   12/2011

OTHER PUBLICATIONS

International Search Report directed to related International Patent Application No. PCT/EP2012/073396, mailed Mar. 5, 2013; 5 pages.
(Continued)

*Primary Examiner* — Gordon J Stock, Jr.
(74) *Attorney, Agent, or Firm* — Sterne, Kessler, Goldstein & Fox P.L.L.C.

(57) ABSTRACT

In the measurement of properties of a wafer substrate, such as Critical Dimension or overlay a sampling plan is produced (2506) defined for measuring a property of a substrate, wherein the sampling plan comprises a plurality of sub-sampling plans. The sampling plan may be constrained to a predetermined fixed number of measurement points and is used (2508) to control an inspection apparatus to perform a plurality of measurements of the property of a plurality of substrates using different sub-sampling plans for respective substrates, optionally, the results are stacked (2510) to at least partially recompose the measurement results according to the sample plan.

16 Claims, 23 Drawing Sheets

(51) Int. Cl.
*G01B 11/14* (2006.01)
*G05B 19/418* (2006.01)
*G03F 7/20* (2006.01)
*G01N 21/956* (2006.01)
*H01L 21/66* (2006.01)

(52) U.S. Cl.
CPC ..... *G01N 21/956* (2013.01); *G01N 21/95607* (2013.01); *G03F 7/70508* (2013.01); *G03F 7/70625* (2013.01); *G03F 7/70633* (2013.01); *G05B 19/41875* (2013.01); *H01L 22/20* (2013.01); *G05B 2219/37224* (2013.01); *Y02P 90/20* (2015.11); *Y02P 90/22* (2015.11)

(58) Field of Classification Search
CPC ........... G01N 21/956; G01N 21/95607; G01N 2021/4711; G01N 2021/4714; G01N 2021/4726; G01N 2021/4728; G01N 2021/4735; G01N 23/20; G03F 7/70508; G03F 7/70625; G03F 7/70633; G05B 19/41875; H01L 22/20; Y02P 90/20; Y02P 90/22
See application file for complete search history.

(56) References Cited

U.S. PATENT DOCUMENTS

| | | | |
|---|---|---|---|
| 6,442,496 B1 | 8/2002 | Pasadyn et al. | |
| 6,650,955 B1 | 11/2003 | Sonderman et al. | |
| 6,687,561 B1* | 2/2004 | Pasadyn | G05B 19/41875 700/109 |
| 6,821,792 B1 | 11/2004 | Sonderman et al. | |
| 7,050,879 B1* | 5/2006 | Wang | G06Q 10/00 438/14 |
| 7,257,502 B1* | 8/2007 | Qu | G03F 7/705 438/7 |
| 7,330,800 B1 | 2/2008 | Good et al. | |
| 7,445,945 B1 | 11/2008 | Markle et al. | |
| 7,460,968 B1* | 12/2008 | Good | G06Q 10/06 700/108 |
| 7,565,254 B2* | 7/2009 | Good | G05B 19/41875 702/83 |
| 7,629,550 B2* | 12/2009 | Asano | G01R 31/2894 209/571 |
| 8,108,060 B2* | 1/2012 | Tsen | G05B 13/048 700/103 |
| 2002/0192966 A1 | 12/2002 | Shanmugasundram et al. | |
| 2004/0169861 A1 | 9/2004 | Mieher et al. | |
| 2005/0033467 A1* | 2/2005 | Purdy | H01L 22/20 700/109 |
| 2006/0074503 A1* | 4/2006 | Purdy | H01L 22/20 700/74 |
| 2006/0074611 A1 | 4/2006 | Wong et al. | |
| 2008/0201117 A1 | 8/2008 | Wong et al. | |
| 2008/0286885 A1 | 11/2008 | Izikson et al. | |
| 2009/0192743 A1 | 7/2009 | Ikeda et al. | |
| 2009/0291510 A1 | 11/2009 | Catlett et al. | |
| 2011/0010000 A1 | 1/2011 | Mos et al. | |
| 2011/0170091 A1 | 7/2011 | Chang et al. | |
| 2011/0202298 A1 | 8/2011 | Izikson et al. | |
| 2012/0084041 A1* | 4/2012 | Izikson | G03F 7/70616 702/113 |
| 2012/0127467 A1* | 5/2012 | Ivanov | G01N 21/6408 356/326 |
| 2013/0035888 A1* | 2/2013 | Kandel | G03F 7/70633 702/81 |
| 2013/0310966 A1* | 11/2013 | MacNaughton | G03F 7/70525 700/121 |

OTHER PUBLICATIONS

International Preliminary Report on Patentability and Written Opinion of the International Searching Authority directed to related International Patent Application No. PCT/EP2012/073396, issued Jun. 24, 2014; 5 pages.

* cited by examiner

METHODS AND APPARATUS FOR MEASURING A PROPERTY OF A SUBSTRATE

CROSS-REFERENCE TO RELATED APPLICATIONS

This application claims the benefit of U.S. provisional application 61/579,969, which was filed on Dec. 23, 2011 and which is incorporated herein in its entirety by reference.

FIELD

The present invention relates to methods of measuring a property of a substrates, such as critical dimension or overlay, using a sampling plan, useable for example in the monitoring of the process of a lithographic or other processing apparatus.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between successive layers formed in or on the patterned substrate and critical linewidth of developed photosensitive resist. This measurement may be performed on a product substrate and/or on a dedicated metrology target. There are various techniques for making measurements of the microscopic structures formed in lithographic processes, including the use of scanning electron microscopes and various specialized tools. A fast and non-invasive form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

To support tighter lithography requirements, accurate correction of the performance of the lithographic apparatus is required. In order to apply more accurate correction functionality, more data/dense sampling of products on a substrate is required to determine a correction set. Using the trade-off between cost of metrology versus accuracy of a correction set, it is common practice that a subset of all products is measured, with the intention to acquire approaching the same level of information as is captured with fully measured products. This is called reduced sampling. Many mathematical approaches exist that support reduced sampling schemes, and these are typically based on geometrical constraints (measurement sites per wafer location).

The effectiveness of a reduced sampling plan to achieve the best accuracy at the lowest possible metrology time/cost is currently determined by a known applied mathematical approach. The applied mathematical approach determines the limitation of the effectiveness of a reduced sampling plan. This is discussed below with reference to FIG. 8.

Current metrology sampling plans are static within a lot of exposed wafer substrates and all measured wafers are sampled with identical sampling plans. Rarely, sampling plans are changed in between lots to adjust for changed state of the exposure and processing equipment. Usually, only a few wafers are measured within each lot to save metrology time and cost.

For CPE (Corrections per Exposure), sometimes wafers are measured with a very dense sampling plan, usually very infrequently (for example once every few weeks).

Problems are:

1) Sampling only a few wafers of each lot may not yield results that are representative for the lot. Wafers outside the regular population that are measured will cause a disturbance in the APC (Advanced Process Control) feedback loop.

2) Wafers outside the regular population may escape detection if not measured.

3) CPE cannot be done very frequently because of the huge metrology cost.

SUMMARY

It is desirable to increase the effectiveness of a sampling plan.

According to an aspect, there is provided an inspection apparatus configured for measuring a property of a plurality of substrates, the inspection apparatus comprising:

an illumination system configured to illuminate a substrate with radiation;

a detection system configured to detect scattered radiation arising from the illumination; and at least one processor configured to:

produce a sampling plan defined for measuring a property of a substrate, wherein the sampling plan comprises a plurality of sub-sampling plans; and control the inspection apparatus to perform a plurality of measurements of the property of a plurality of substrates using different sub-sampling plans for respective substrates.

According to an aspect, there is provided a lithography apparatus comprising an exposure system and an inspection apparatus according to any previous claim, the lithography apparatus comprising at least one processor configured to:

control the exposure system to expose the plurality of substrates prior to controlling the inspection apparatus to perform the plurality of measurements of the property of the plurality of substrates; and control the exposure system to process a subsequent at least one substrate with conditions based on the plurality of measurements.

According to an aspect, there is provided a method of measuring a property of a substrate, the method comprising the steps:

defining a sampling plan for measuring a property of a substrate;

updating the sampling plan separately in two or more coordinates; and measuring the property of a substrate using the updated sampling plan.

According to an aspect, there is provided a method of measuring a property of a substrate, the method comprising the steps:

defining a sampling plan for measuring a property of a substrate;

recording process setup information and processing the substrate using a processing apparatus according to the process setup information;

updating the sampling plan based on the process setup information; and measuring the property of a substrate using the updated sampling plan.

According to an aspect, there is provided a method of measuring a property of a substrate, the method comprising the steps:

defining a sampling plan for measuring a property of a substrate;

measuring processing data related to processing of the substrate using a processing apparatus;

determining the variation of the processing data;

updating the sampling plan based on the variation of the processing data; and measuring the property of a substrate using the updated sampling plan, wherein updating the sampling plan comprises modifying the sampling across a substrate.

According to an aspect, there is provided a method of measuring a property of a substrate, the method comprising the steps:

defining a sampling plan for measuring a property of a substrate;

measuring processing data related to processing of the substrate using a processing apparatus;

measuring the property of a substrate;

determining the correlation of the measured processing data with the measured property;

updating the sampling plan based on the correlation of the processing data with the measured property; and measuring the property of a substrate using the updated sampling plan.

According to an aspect, there is provided a method of measuring a property of a substrate, the method comprising the steps:

defining a sampling plan for measuring a property of a substrate;

measuring an angularly resolved spectrum of a substrate;

determining the variation of the angularly resolved spectrum;

updating the sampling plan based on the variation of the angularly resolved spectrum; and measuring the property of a substrate using the updated sampling plan.

According to an aspect, there is provided a method of measuring a property of a plurality of substrates, the method comprising the steps:

defining a sampling plan for measuring a property of a substrate;

decomposing the sampling plan into a plurality of sub-sampling plans;

performing a plurality of measurements of the property of a plurality of substrates using different sub-sampling plans on respective substrates; and stacking the results of the plurality of measurements to at least partially recompose measurement results according to the sampling plan.

According to an aspect, there is provided a method of measuring a property of a substrate, the method comprising the steps:

defining a sampling plan for measuring a property of a substrate;

measuring the property of a substrate;

determining position-dependent variance of the measured property;

updating the sampling plan based on the position-dependent variance of the measured property; and measuring the property of a substrate using the updated sampling plan.

According to an aspect, there is provided an inspection apparatus configured for measuring a property of a substrate, the inspection apparatus comprising:

an illumination system configured to illuminate a substrate with radiation;

a detection system configured to detect scattering properties arising from the illumination; and a processor configured to:
  receive a sampling plan defined for measuring a property of a substrate;
  update the sampling plan separately in two or more coordinates; and
  control the inspection apparatus to measure the property of a substrate using the updated sampling plan.

According to an aspect, there is provided an inspection apparatus configured for measuring a property of a substrate, the inspection apparatus comprising:

an illumination system configured to illuminate a substrate with radiation;

a detection system configured to detect scattering properties arising from the illumination; and a processor configured to:
  receive a sampling plan defined for measuring a property of a substrate;
  receive recorded process setup information related to processing of the substrate using a processing apparatus;
  update the sampling plan based on the process setup information; and
  control the inspection apparatus to measure the property of a substrate using the updated sampling plan.

According to an aspect, there is provided an inspection apparatus configured for measuring a property of a substrate, the inspection apparatus comprising:

an illumination system configured to illuminate a substrate with radiation;

a detection system configured to detect scattering properties arising from the illumination; and a processor configured to:
  receive a sampling plan defined for measuring a property of a substrate;

receive recorded processing data related to processing of the substrate using a processing apparatus;

determine the variation of the processing data;

update the sampling plan based on the variation of the processing data; and the inspection apparatus to measure the property of a substrate using the updated sampling plan, wherein the processor is configured to update the sampling plan by modifying the sampling across a substrate.

According to an aspect, there is provided an inspection apparatus configured for measuring a property of a substrate, the inspection apparatus comprising:

an illumination system configured to illuminate a substrate with radiation;

a detection system configured to detect scattering properties arising from the illumination; and a processor configured to:

receive a sampling plan defined for measuring a property of a substrate;

receive recorded processing data related to processing of the substrate using a processing apparatus;

control the inspection apparatus to measure the property of a substrate;

determine the correlation of the measured processing data with the measured property;

update the sampling plan based on the correlation of the processing data with the measured property; and measure the property of a substrate using the updated sampling plan.

According to an aspect, there is provided an inspection apparatus configured for measuring a property of a substrate, the inspection apparatus comprising:

an illumination system configured to illuminate a substrate with radiation;

a detection system configured to detect scattering properties arising from the illumination; and a processor configured to:

receive a sampling plan defined for measuring a property of a substrate;

control the inspection apparatus to measure an angularly resolved spectrum of a substrate;

determine the variation of the angularly resolved spectrum;

update the sampling plan based on the variation of the angularly resolved spectrum; and control the inspection apparatus to measure the property of a substrate using the updated sampling plan.

According to an aspect, there is provided an inspection apparatus configured for measuring a property of a substrate, the inspection apparatus comprising:

an illumination system configured to illuminate a substrate with radiation;

a detection system configured to detect scattering properties arising from the illumination; and a processor configured to:

receive a sampling plan defined for measuring a property of a substrate;

decompose the sampling plan into a plurality of sub-sampling plans;

control the inspection apparatus to perform a plurality of measurements of the property of a plurality of substrates using different sub-sampling plans on respective substrates; and stack the results of the plurality of measurements to at least partially recompose measurement results according to the sampling plan.

According to an aspect, there is provided an inspection apparatus configured for measuring a property of a substrate, the inspection apparatus comprising:

an illumination system configured to illuminate a substrate with radiation;

a detection system configured to detect scattering properties arising from the illumination; and a processor configured to:

receive a sampling plan defined for measuring a property of a substrate;

control the inspection apparatus to measure the property of a substrate;

determine position-dependent variance of the measured property;

update the sampling plan based on the position-dependent variance of the measured property; and measure the property of a substrate using the updated sampling plan.

According to an aspect, there is provided a lithography apparatus comprising an exposure system and an inspection apparatus, the inspection apparatus configured for measuring a property of a substrate and the inspection apparatus comprising:

an illumination system configured to illuminate a substrate with radiation;

a detection system configured to detect scattering properties arising from the illumination; and a processor configured to:

receive a sampling plan defined for measuring a property of a substrate;

update the sampling plan separately in two or more coordinates; and control the inspection apparatus to measure the property of a substrate using the updated sampling plan.

According to an aspect, there is provided a lithographic cell comprising: a lithographic apparatus comprising an exposure system; and an inspection apparatus, the inspection apparatus configured for measuring a property of a substrate and the inspection apparatus comprising:

an illumination system configured to illuminate a substrate with radiation;

a detection system configured to detect scattering properties arising from the illumination; and a processor configured to:

receive a sampling plan defined for measuring a property of a substrate;

update the sampling plan separately in two or more coordinates; and control the inspection apparatus to measure the property of a substrate using the updated sampling plan.

According to an aspect, there is provided a lithography apparatus comprising an exposure system and an inspection apparatus, the inspection apparatus configured for measuring a property of a substrate and the inspection apparatus comprising:

an illumination system configured to illuminate a substrate with radiation;

a detection system configured to detect scattering properties arising from the illumination; and a processor configured to:

receive a sampling plan defined for measuring a property of a substrate;

receive recorded process setup information related to processing of the substrate using a processing apparatus;

update the sampling plan based on the process setup information; and control the inspection apparatus to measure the property of a substrate using the updated sampling plan.

According to an aspect, there is provided a lithographic cell comprising: a lithographic apparatus comprising an exposure system; and an inspection apparatus, the inspection apparatus configured for measuring a property of a substrate and the inspection apparatus comprising:

an illumination system configured to illuminate a substrate with radiation;

a detection system configured to detect scattering properties arising from the illumination; and a processor configured to:

receive a sampling plan defined for measuring a property of a substrate;

receive recorded process setup information related to processing of the substrate using a processing apparatus;

update the sampling plan based on the process setup information; and control the inspection apparatus to measure the property of a substrate using the updated sampling plan.

According to an aspect, there is provided a lithography apparatus comprising an exposure system and an inspection apparatus, the inspection apparatus configured for measuring a property of a substrate and the inspection apparatus comprising:

an illumination system configured to illuminate a substrate with radiation;

a detection system configured to detect scattering properties arising from the illumination; and a processor configured to:

receive a sampling plan defined for measuring a property of a substrate;

receive recorded processing data related to processing of the substrate using a processing apparatus;

determine the variation of the processing data;

update the sampling plan based on the variation of the processing data; and control the inspection apparatus to measure the property of a substrate using the updated sampling plan, wherein the processor is configured to update the sampling plan by modifying the sampling across a substrate.

According to an aspect, there is provided a lithographic cell comprising: a lithographic apparatus comprising an exposure system; and an inspection apparatus, the inspection apparatus configured for measuring a property of a substrate and the inspection apparatus comprising:

an illumination system configured to illuminate a substrate with radiation;

a detection system configured to detect scattering properties arising from the illumination; and a processor configured to:

receive a sampling plan defined for measuring a property of a substrate;

receive recorded processing data related to processing of the substrate using a processing apparatus;

determine the variation of the processing data;

update the sampling plan based on the variation of the processing data; and control the inspection apparatus to measure the property of a substrate using the updated sampling plan, wherein the processor is configured to update the sampling plan by modifying the sampling across a substrate.

According to an aspect, there is provided a lithography apparatus comprising an exposure system and an inspection apparatus, the inspection apparatus configured for measuring a property of a substrate and the inspection apparatus comprising:

an illumination system configured to illuminate a substrate with radiation;

a detection system configured to detect scattering properties arising from the illumination; and a processor configured to:

receive a sampling plan defined for measuring a property of a substrate;

receive recorded processing data related to processing of the substrate using a processing apparatus;

control the inspection apparatus to measure the property of a substrate;

determine the correlation of the measured processing data with the measured property;

update the sampling plan based on the correlation of the processing data with the measured property; and measuring the property of a substrate using the updated sampling plan.

According to an aspect, there is provided a lithographic cell comprising: a lithographic apparatus comprising an exposure system; and an inspection apparatus, the inspection apparatus configured for measuring a property of a substrate and the inspection apparatus comprising:

an illumination system configured to illuminate a substrate with radiation;

a detection system configured to detect scattering properties arising from the illumination; and a processor configured to:

receive a sampling plan defined for measuring a property of a substrate;

receive recorded processing data related to processing of the substrate using a processing apparatus;

control the inspection apparatus to measure the property of a substrate;

determine the correlation of the measured processing data with the measured property;

update the sampling plan based on the correlation of the processing data with the measured property; and measure the property of a substrate using the updated sampling plan.

According to an aspect, there is provided a lithography apparatus comprising an exposure system and an inspection apparatus, the inspection apparatus configured for measuring a property of a substrate and the inspection apparatus comprising:

an illumination system configured to illuminate a substrate with radiation;

a detection system configured to detect scattering properties arising from the illumination; and a processor configured to:

receive a sampling plan defined for measuring a property of a substrate;

control the inspection apparatus to measure an angularly resolved spectrum of a substrate;

determine the variation of the angularly resolved spectrum;

update the sampling plan based on the variation of the angularly resolved spectrum; and control the inspection apparatus to measure the property of a substrate using the updated sampling plan.

According to an aspect, there is provided a lithographic cell comprising: a lithographic apparatus comprising an exposure system; and an inspection apparatus, the inspection apparatus configured for measuring a property of a substrate and the inspection apparatus comprising:

an illumination system configured to illuminate a substrate with radiation;

a detection system configured to detect scattering properties arising from the illumination; and a processor configured to:

receive a sampling plan defined for measuring a property of a substrate;

control the inspection apparatus to measure an angularly resolved spectrum of a substrate;

determine the variation of the angularly resolved spectrum;

update the sampling plan based on the variation of the angularly resolved spectrum; and control the inspection apparatus to measure the property of a substrate using the updated sampling plan.

According to an aspect, there is provided a lithography apparatus comprising an exposure system and an inspection apparatus, the inspection apparatus configured for measuring a property of a substrate and the inspection apparatus comprising:

an illumination system configured to illuminate a substrate with radiation;

a detection system configured to detect scattering properties arising from the illumination; and a processor configured to:

receive a sampling plan defined for measuring a property of a substrate;

decompose the sampling plan into a plurality of sub-sampling plans;

control the inspection apparatus to perform a plurality of measurements of the property of a plurality of substrates using different sub-sampling plans on respective substrates; and stack the results of the plurality of measurements to at least partially recompose measurement results according to the sampling plan.

According to an aspect, there is provided a lithographic cell comprising: a lithographic apparatus comprising an exposure system; and an inspection apparatus, the inspection apparatus configured for measuring a property of a substrate and the inspection apparatus comprising:

an illumination system configured to illuminate a substrate with radiation;

a detection system configured to detect scattering properties arising from the illumination; and a processor configured to:

receive a sampling plan defined for measuring a property of a substrate;

decompose the sampling plan into a plurality of sub-sampling plans;

control the inspection apparatus to perform a plurality of measurements of the property of a plurality of substrates using different sub-sampling plans on respective substrates; and stack the results of the plurality of measurements to at least partially recompose measurement results according to the sampling plan.

According to an aspect, there is provided a lithography apparatus comprising an exposure system and an inspection apparatus, the inspection apparatus configured for measuring a property of a substrate and the inspection apparatus comprising:

an illumination system configured to illuminate a substrate with radiation;

a detection system configured to detect scattering properties arising from the illumination; and a processor configured to:

control the inspection apparatus to measure the property of a substrate;

determine position-dependent variance of the measured property;

update the sampling plan based on the position-dependent variance of the measured property; and measuring the property of a substrate using the updated sampling plan.

According to an aspect, there is provided a lithographic cell comprising: a lithographic apparatus comprising an exposure system; and an inspection apparatus, the inspection apparatus configured for measuring a property of a substrate and the inspection apparatus comprising:

an illumination system configured to illuminate a substrate with radiation;

a detection system configured to detect scattering properties arising from the illumination; and a processor configured to:

receive a sampling plan defined for measuring a property of a substrate;

control the inspection apparatus to measure the property of a substrate;

determine position-dependent variance of the measured property;

update the sampling plan based on the position-dependent variance of the measured property; and measuring the property of a substrate using the updated sampling plan.

According to an aspect, there is provided a computer program product containing one or more sequences of machine-readable instructions for measuring a property of a substrate, the instructions being adapted to cause one or more processors to perform a method or steps according to any of the aspects.

BRIEF DESCRIPTION OF THE DRAWINGS

Embodiments will now be described, by way of example only, with reference to the accompanying schematic drawings in which corresponding reference symbols indicate corresponding parts, and in which.

DETAILED DESCRIPTION

Figure 1:
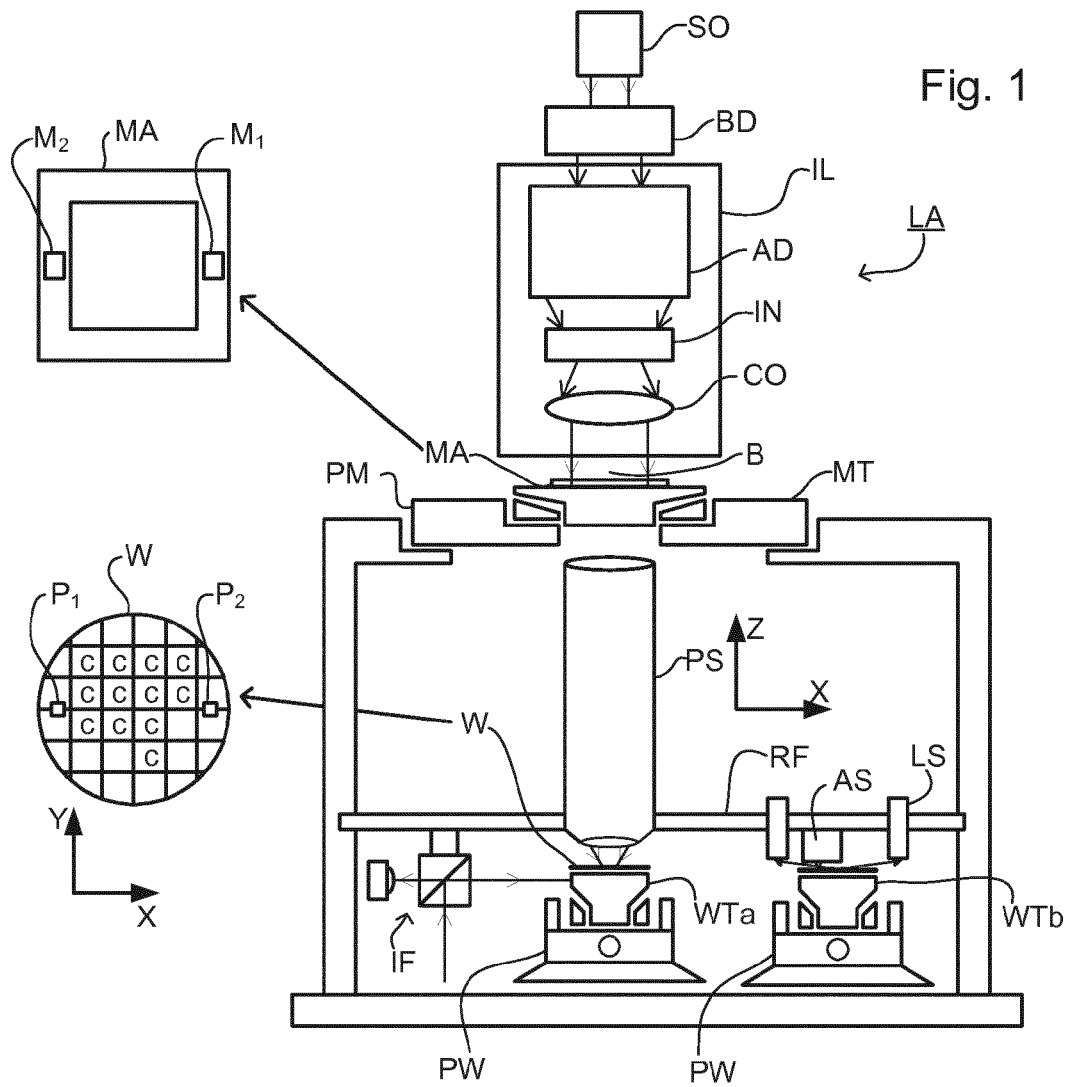
FIG. 1 depicts a lithographic apparatus.

FIG. 1 schematically depicts a lithographic apparatus. The apparatus comprises:

an illumination system (illuminator) IL configured to condition a radiation beam B (e.g. UV radiation or Extreme UV (EUV) radiation).

a support structure (e.g. a mask table) MT constructed to support a patterning device (e.g. a mask) MA and connected to a first positioner PM configured to accurately position the patterning device in accordance with certain parameters;

a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PS configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF (e.g. an interferometric device, linear encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above. Combinations and/or variations on the above described modes of use or entirely different modes of use may also be employed.

Figure 2:
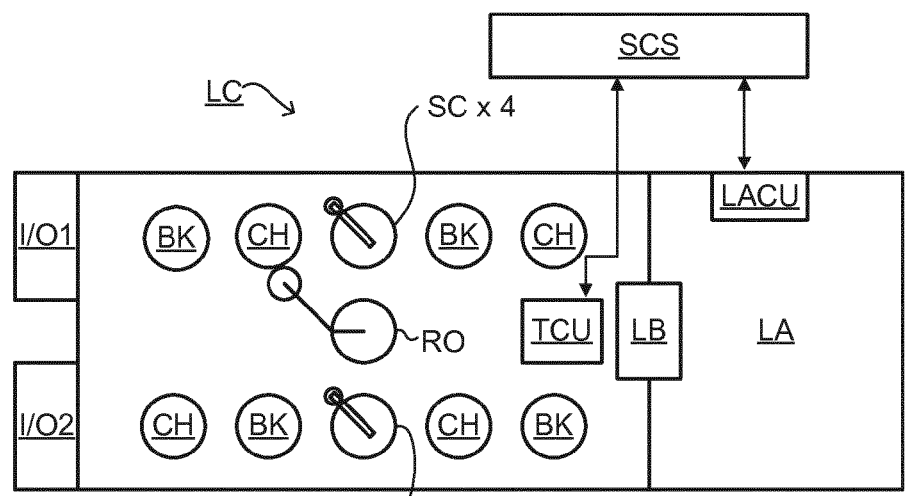
FIG. 2 depicts a lithographic cell or cluster including the apparatus of FIG. 1.

FIG. 2 depicts a lithographic cell or cluster including the apparatus of FIG. 1. As shown in FIG. 2, the lithographic apparatus LA forms part of a lithographic cell LC, also sometimes referred to a 'lithocell' or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked— to improve yield—or discarded, thereby avoiding performing exposures on substrates that are known to be faulty. In a case where only some target portions of a substrate are faulty, further exposures can be performed only on those target portions which are good.

An inspection apparatus or metrology tool is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
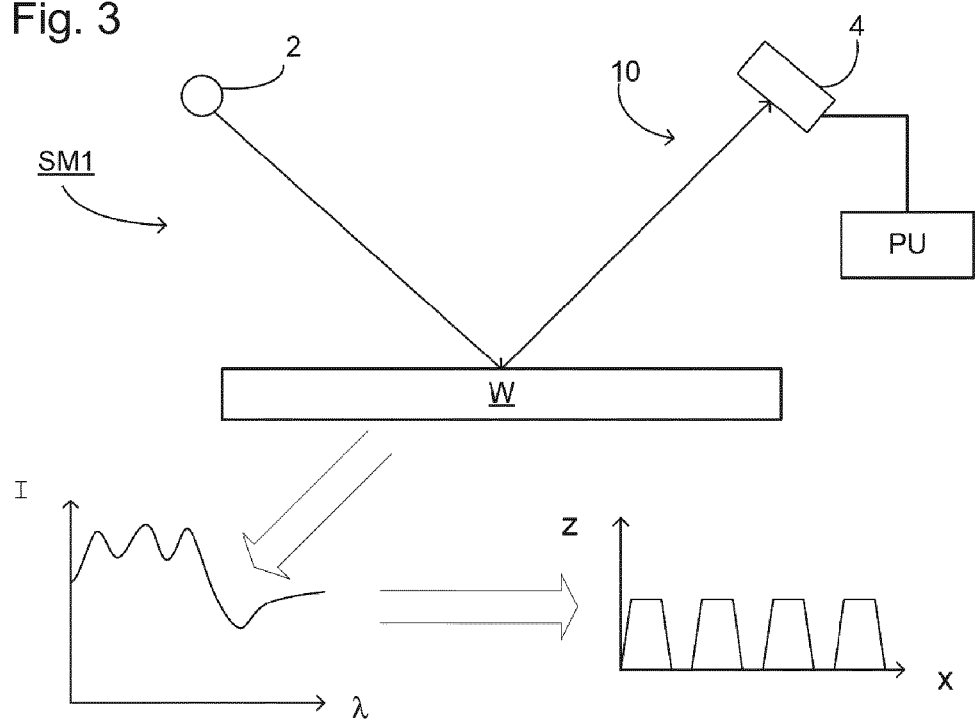
FIG. 3 depicts a first scatterometer.

FIG. 3 depicts a scatterometer. It comprises a broadband (white light) radiation projector 2 which projects radiation onto a substrate W. The reflected radiation is passed to a spectrometer detector 4, which measures a spectrum 10 (intensity as a function of wavelength) of the specular reflected radiation. From this data, the structure or profile giving rise to the detected spectrum may be reconstructed by processing unit PU, e.g. by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
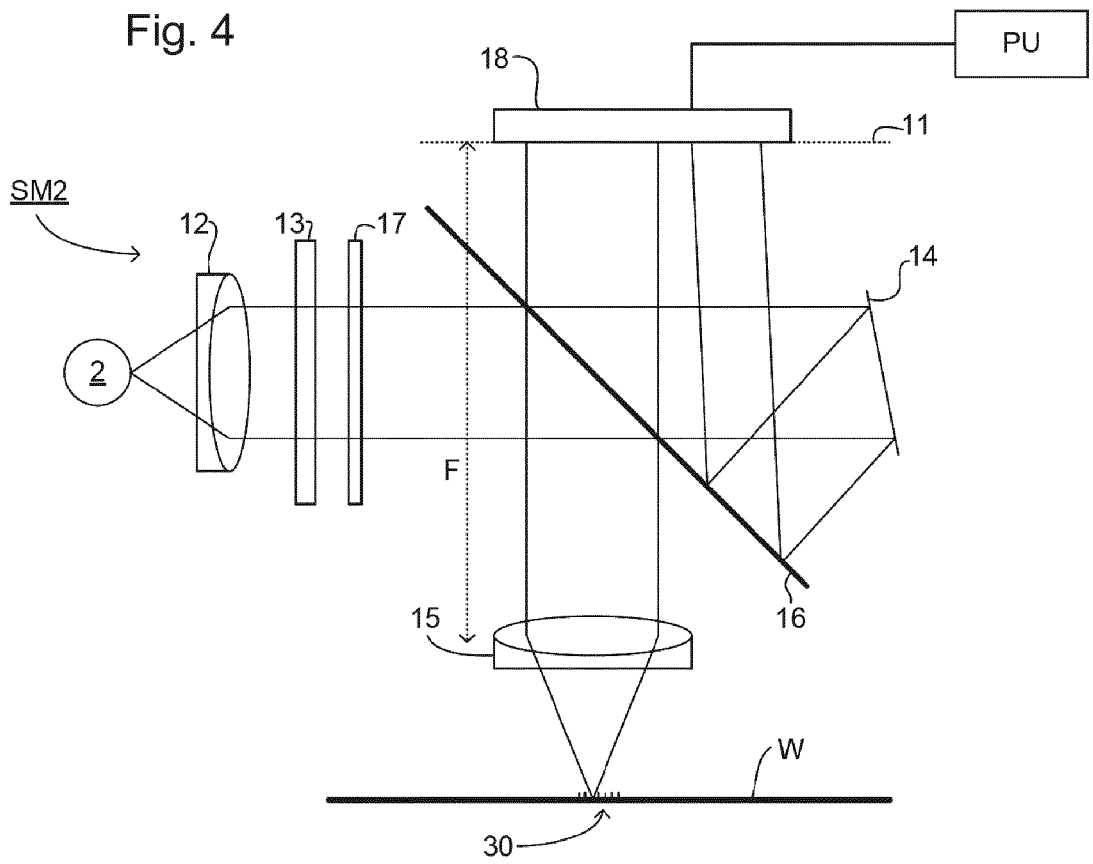
FIG. 4 depicts a second scatterometer.

Another scatterometer is shown in FIG. 4. In this device, the radiation emitted by radiation source 2 is collimated using lens system 12 and transmitted through interference filter 13 and polarizer 17, reflected by partially reflected surface 16 and is focused onto substrate W via a microscope objective lens 15, which has a high numerical aperture (NA), preferably at least 0.9 and more preferably at least 0.95. Immersion scatterometers may even have lenses with numerical apertures over 1. The reflected radiation then transmits through partially reflecting surface 16 into a detector 18 in order to have the scatter spectrum detected. The detector may be located in the back-projected pupil plane 11, which is at the focal length of the lens system 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured.

The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18 or alternatively on to a different detector (not shown).

A set of interference filters 13 is available to select a wavelength of interest in the range of, say, 405-790 nm or even lower, such as 200-300 nm. The interference filter may be tunable rather than comprising a set of different filters. A grating could be used instead of interference filters.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Using a broadband light source (i.e. one with a wide range of light frequencies or wavelengths—and therefore of colors) is possible, which gives a large etendue, allowing the mixing of multiple wavelengths. The plurality of wavelengths in the broadband preferably each has a bandwidth of $\Delta\lambda$ and a spacing of at least 2 $\Delta\lambda$ (i.e. twice the bandwidth). Several "sources" of radiation can be different portions of an extended radiation source which have been split using fiber bundles. In this way, angle resolved scatter spectra can be measured at multiple wavelengths in parallel. A 3-D spectrum (wavelength and two different angles) can be measured, which contains more information than a 2-D spectrum. This allows more information to be measured which increases metrology process robustness. This is described in more detail in EP1,628,164A.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

A key component of accurate lithography is an ability to calibrate individual lithographic apparatus. In addition to general parameters affecting the whole substrate area, it is known to map and model the error 'fingerprint' of an individual apparatus across the substrate area. This fingerprint, which can be established in terms of focus, dose and/or alignment, can be used during exposure to correct the idiosyncrasies of that apparatus, and thereby achieve a more accurate patterning.

Improvements to the apparatus's focus and overlay (layer-to-layer alignment) uniformity have recently been achieved by the applicant's Baseliner™ scanner stability module, leading to an optimized process window for a given feature size and chip application, enabling the continuation the creation of smaller, more advanced chips. The scanner stability module may automatically reset the system to a pre-defined baseline each day. To do this it retrieves standard measurements taken from a monitor wafer using a metrology tool. The monitor wafer is exposed using a special reticle containing special scatterometry marks. From that day's measurements, the scanner stability module determines how far the system has drifted from its baseline. It then calculates wafer-level overlay and focus correction sets. The lithography system then converts these correction sets into specific corrections for each exposure on subsequent production wafers.

Figure 5:
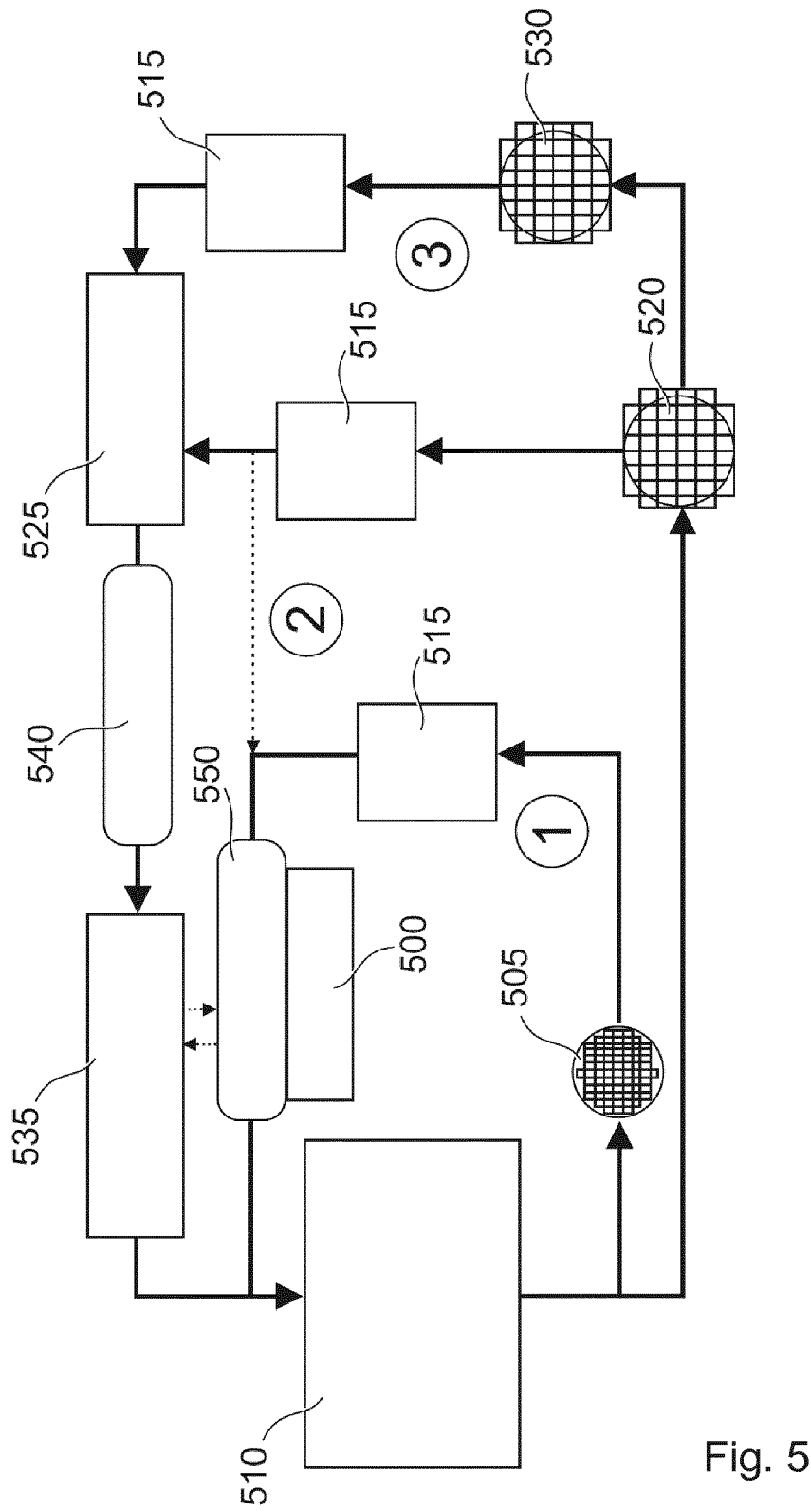
FIG. 5 is a schematic diagram of control mechanisms in a lithographic process utilizing a scanner stability module.

FIG. 5 depicts the overall lithography and metrology method incorporating the scanner stability module 500 (essentially an application running on a server, in this example). Shown are three main process control loops. The first loop provides the local scanner control using the scanner stability module 500 and monitor wafers. The monitor wafer 505 is shown being passed from the main lithography unit 510, having been exposed to set the baseline parameters for focus and overlay. At a later time, metrology tool 515 reads these baseline parameters, which are then interpreted by the scanner stability module 500 so as to calculate correction routines so as to provide scanner feedback 550, which is passed to the main lithography unit 510, and used when performing further exposures.

The second Advanced Process Control (APC) loop is for local scanner control on-product (determining focus, dose, and overlay). The exposed product wafer 520 is passed to metrology tool 515 where information relating to the critical dimensions, sidewall angles and overlay is determined and passed onto the Advanced Process Control (APC) module 525. This data is also passed to the scanner stability module 500. Process corrections 540 are made before the Manufacturing Execution System (MES) 535 takes over, providing scanner control to the main lithography unit 510, in communication with the scanner stability module 500.

The third loop is to allow metrology integration into the second APC loop (e.g. for double patterning). The post etched wafer 530 is passed to metrology tool 515 which again passes information relating to the critical dimensions, sidewall angles and overlay, read from the wafer, to the Advanced Process Control (APC) module. The loop continues the same as with the second loop.

Figure 6:
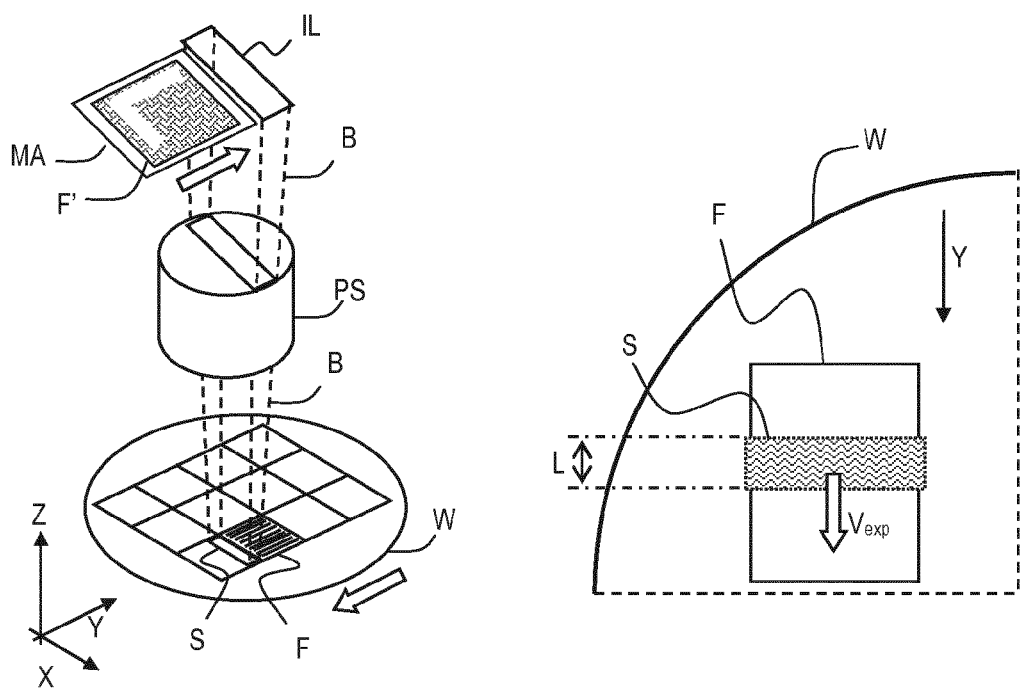
FIG. 6 illustrates schematically the operation of the apparatus of FIG. 1 in exposing a target portion (field) on a substrate.

FIG. 6 illustrates schematically the scanning operation to expose one field F on a substrate W in the lithographic apparatus of FIG. 1. The substrate W and mask MA are seen in perspective view, with the illumination source IL above and the projection system PS in between. Mask MA carries a transparent pattern F' which is a scaled up version of the pattern to be applied to one field F on substrate W. Illumination source IL presents a slit of radiation S', not large enough in the Y direction to cover the area F' but wide enough in the X direction. To expose the entire field, the mask MA is moved through the area of slit S' to project a corresponding slit area S on substrate field F. These movements are represented by large arrows.

Conceptually, it is sufficient to regard the substrate as staying still, while the patterned slit S passes over it in the opposite sense of the Y direction, as shown by the schematic plan detail to the right of the diagram. The slit with length L is moved with an exposure velocity Vexp over field F.

Parameters of the projection system PS and control set points are adjusted prior to exposure to ensure that distortion within the slit is constant over the whole exposure. Certain parameters, for example focus set points, may be controlled dynamically throughout the scanning movement, to maintain optimum, uniform patterning quality across the field.

Figure 7:
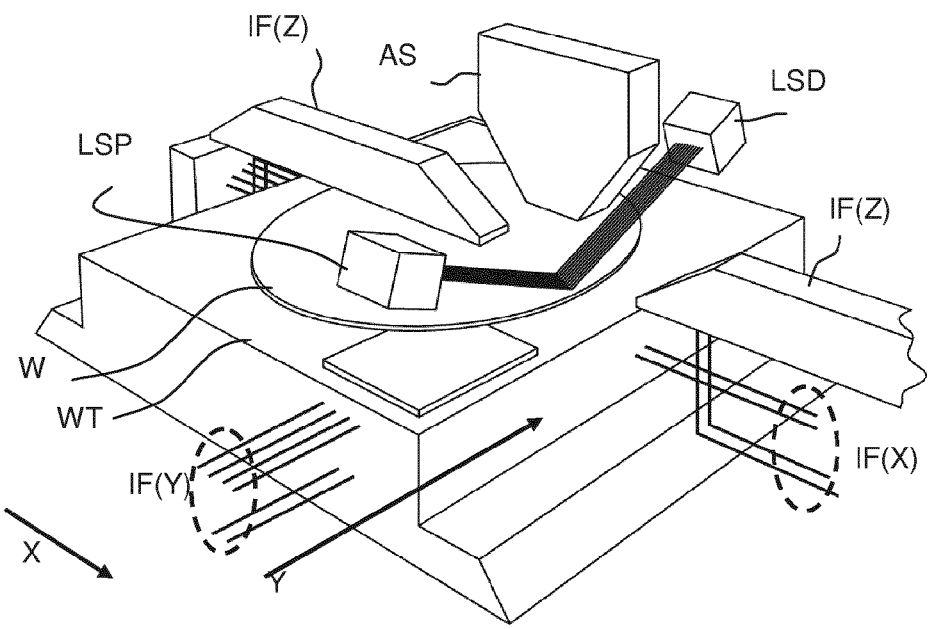
FIG. 7 illustrates a level sensor apparatus in the lithography apparatus of FIG. 1.

FIG. 7 is a perspective view of level mapping operations taking place in a lithographic apparatus. Substrate table WT is shown with a substrate W loaded thereon which is being measured by a level sensor comprising a level sensing projector LSP and a level sensing detector LSD. An alignment sensor AS is provided for measuring X-Y position across the substrate. Position sensor IF, seen in FIG. 1, is seen in more detail in FIG. 4. A pair of Z-direction position sensors IF(Z) are provided (in this example, interferometers), while IF(X) represents rays of the X-direction interferometer, and IF(Y) represents rays of the Y-direction interferometer. Other forms of position sensor may be used, for example, encoder plates, as is known to the skilled person.

In operation of the level sensor, a number of level sensing "spots" are projected onto a line-shaped portion of the substrate surface, by projector LSP, and reflected from the substrate surface to be imaged in the level sensing detector LSD.

Figure 8:
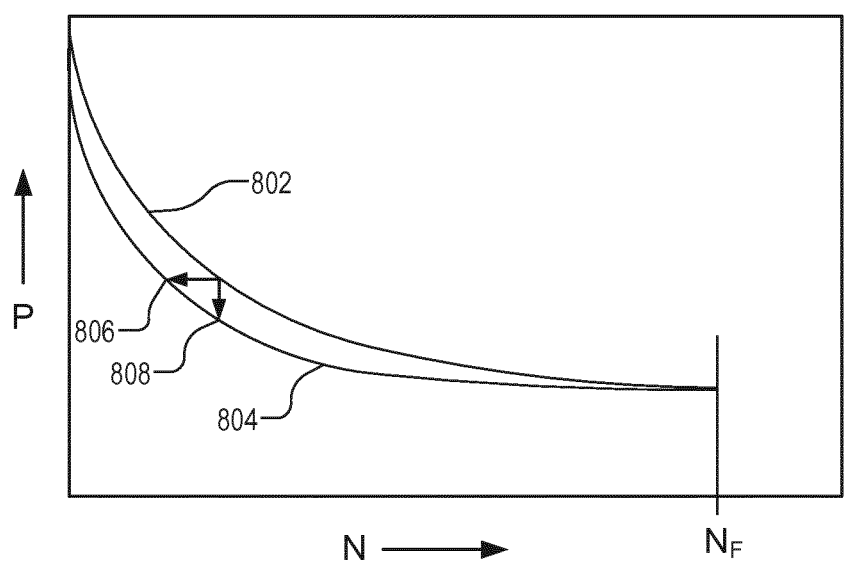
FIG. 8 is a graph illustrating the effectiveness of reduced sampling.

FIG. 8 is a graph illustrating the effectiveness of reduced sampling.

The vertical axis, P, is the performance metric after correction, for example overlay residuals. The horizontal axis, N, is the number of measurement points in the sampling plan used for determination of the corrections. Better performance is a lower value of P, which is typically achieved by increasing the number of sample points N. $N_F$ is the number of measurement points at which the wafer is fully measured, which gives the best performance, at the cost of time consuming sampling. The curve 802 is the optimal curve based on geometric constraints.

Embodiments described herein improve the effectiveness of reduced sampling to provide an improved curve 804, such that faster measurements (with fewer measurement points) are achievable 806 for the same performance, or better performance is achieved 808 for the same measurement time.

Figure 9:
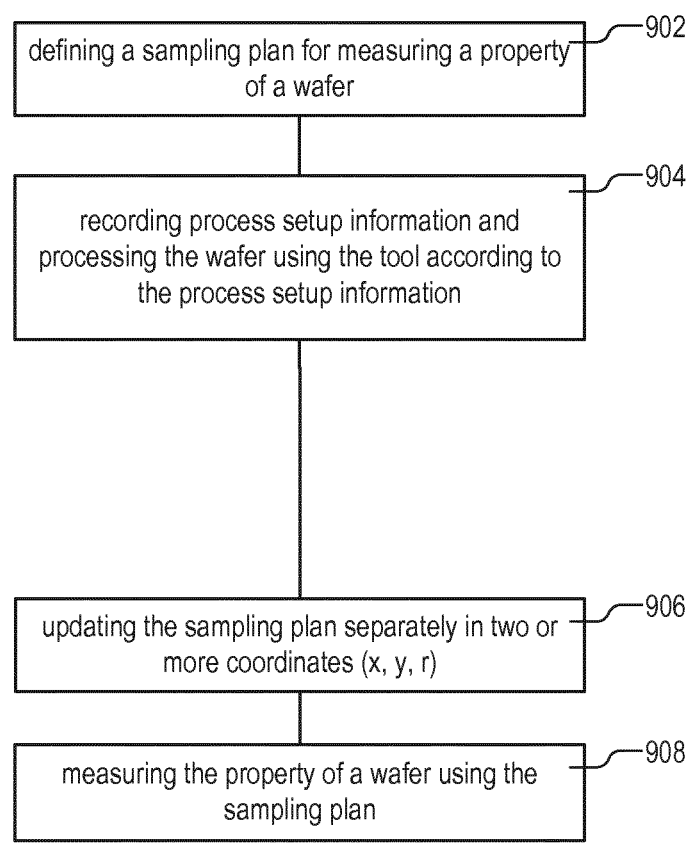
FIG. 9 is a flowchart illustrating an embodiment with the sampling plan updated separately in two or more coordinates.

FIG. 9 is a flowchart illustrating an embodiment with the sampling plan updated separately in two or more coordinates. In this embodiment, the approach is to update sampling schemes separately for x, y and/or r (radius) within one process layer. The particular scheme is determined by application (for example, it can be x or y only, or summation/highest/lowest x or y per area, or per radius). Implementation can be via segmented metrology targets, which are dedicated either to x or y. The motivations of this approach include:

1) scanner and/or metrology equipment have different budgets for x and y, therefore the noise contribution in x, y will be different leading to a delta in required sampling for similar model uncertainty;

2) in the case of double exposure (split in x, y, also known as gridded design), with reference to different layers the overlay requirements for x, y are different, therefore the required model uncertainty will be different; and 3) different process influences in x, y, for instance CMP (Chemical Mechanical Polishing/Planarization) or annealing steps produce local radial fingerprints where the model uncertainty is quite different in x versus y. This can, but does not have to, be expressed by a radial function as well.

The steps in this embodiment include:

902—defining a sampling plan for measuring a property of a wafer.

904—recording process setup information and processing the wafer using the scanner tool according to the process setup information. The process setup information may include parameters of the projection system PS illustrated in FIG. 6 and exposure and focus control set points. The process setup information may relate to other processing apparatus rather than scanners, for example other lithographic apparatus or etching apparatus. Thus the embodiments described herein are not limited to lithography apparatus.

906—updating the sampling plan separately in two or more coordinates. If step 904 is performed, this updating of the sampling plan is based on the recorded process setup information. The updating of the sampling plan may include modifying the sampling across a wafer, for example by changing the sampling density and/or locations within the wafer, based for example upon the recorded process setup information.

908—measuring the property of a wafer using the updated sampling plan.

Alternatively to using step 904 and in step 906 updating the sampling plan based on process setup information, the method may include steps as described with reference to FIG. 11:

measuring processing data related to processing of the wafer using a scanner; and determining the variation of the processing data, and the updating of the sampling plan in step 906 is based on the variation of the processing data.

Alternatively to using step 904 and in step 906 updating the sampling plan based on process setup information, the method may include steps as described with reference to FIG. 12:

measuring processing data related to processing of the wafer using a scanner;

measuring the property of a substrate; and determining the correlation of the processing data with the property, and the updating of the sampling plan in step 906 is based on the correlation of the processing data with the property.

Figure 10:
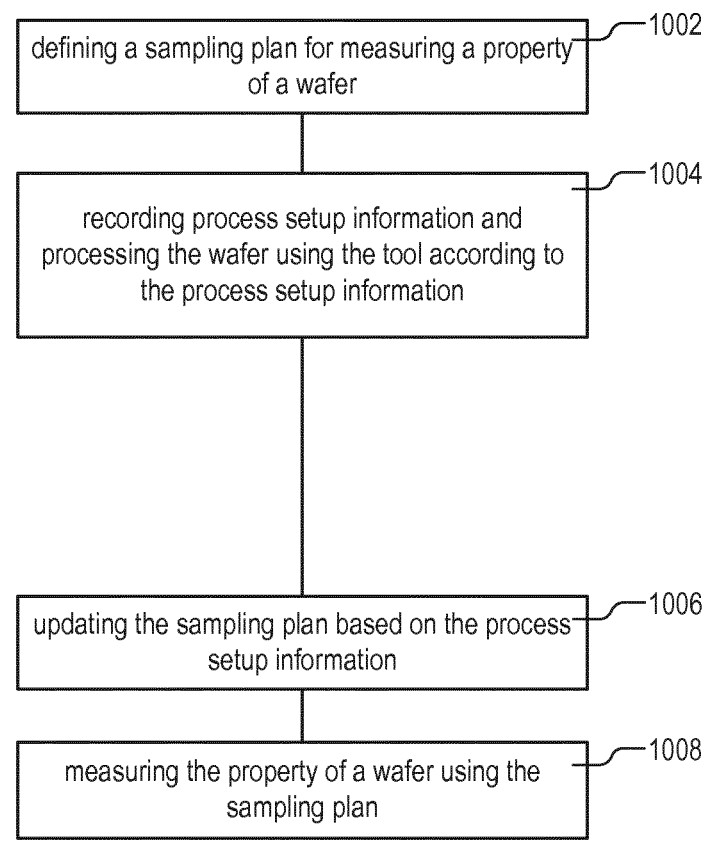
FIG. 10 is a flowchart illustrating an embodiment with the sampling plan updated based on process setup information.

FIG. 10 is a flowchart illustrating an embodiment with the sampling plan updated based on process setup information. In this embodiment, determination of a sampling plan may make use of constraints based on scanner (process job) information (for example scan direction, which chuck is used in a twin wafer chuck lithography apparatus, wafer layout) or actuator information (for example number of fingers that can be actuated to define the illumination dose in a scanner). The process setup information may thus include parameters of the projection system PS illustrated in FIG. 6 and exposure and focus control set points.

The steps in this embodiment include:

1002—defining a sampling plan for measuring a property of a wafer.

1004—recording process setup information and processing the wafer using the scanner tool according to the process setup information. The process setup information may for example comprise scanner process job information or scanner actuator information. The process setup information may relate to other processing apparatus (tools) rather than scanners, for example other lithographic apparatus or etching apparatus.

1006—updating the sampling plan based on the process setup information. The updating of the sampling plan may include modifying the sampling across a wafer, for example by changing the sampling density and/or locations within the wafer, based for example upon the recorded process setup information.

1008—measuring the property of a wafer using the updated sampling plan.

Figure 11:
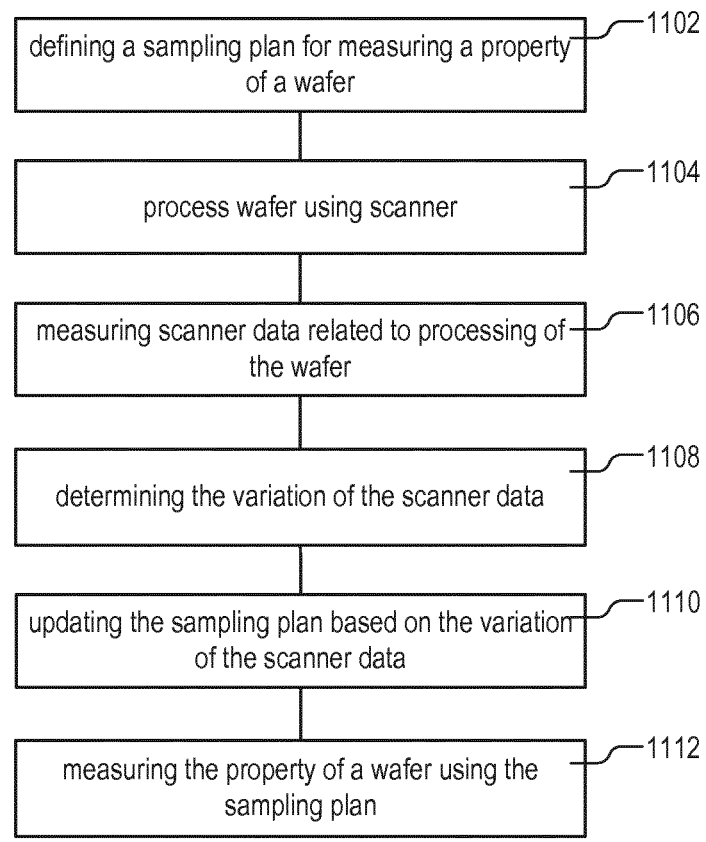
FIG. 11 is a flowchart illustrating an embodiment with the sampling plan updated based on variation of measured scanner data.

FIG. 11 is a flowchart illustrating an embodiment with the sampling plan updated based on variation of measured scanner data. In this embodiment, the approach is determination of a sampling plan by analyzing alignment data/leveling data of a similar or the same wafer, where homogeneity or uncertainty per area/wafer can be classified. For example an area with a large variation in MCC (multiple correlation coefficient)/WQ (wafer quality) or topology requires denser sampling. The approach of an embodiment is to monitor fingerprints of alignment data/leveling data and increase sampling on locations where fingerprint changes are detected.

The steps include:

1102—defining a sampling plan for measuring a property of a wafer.

1104—processing a wafer using the scanner.

1106—measuring processing data related to processing of the wafer using a scanner. The processing data may for example comprise alignment data and/or leveling data.

1108—determining the variation of the processing data.

1110—updating the sampling plan based on the variation of the processing data. Updating the sampling plan includes modifying the sampling across a wafer, for example by changing the sampling density and/or locations within the wafer, based for example upon the variation of the processing data.

1112—measuring the property of a wafer using the updated sampling plan.

Figure 12:
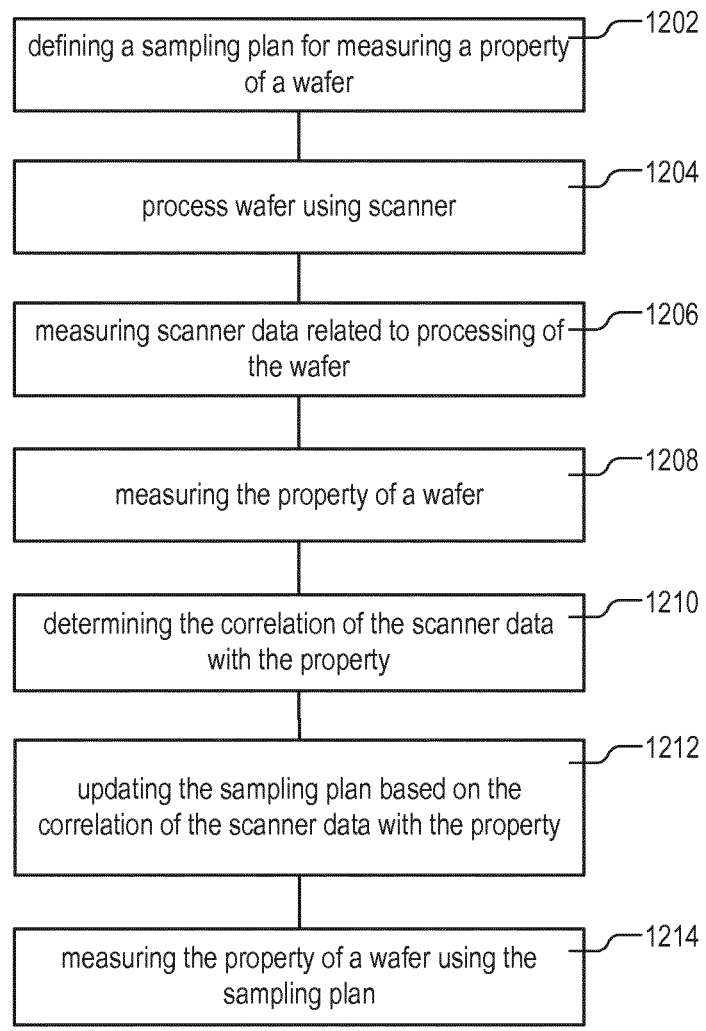
FIG. 12 is a flowchart illustrating an embodiment with the sampling plan updated based on correlation of measured scanner data with the property being measured according to the sample plan.

FIG. 12 is a flowchart illustrating an embodiment with the sampling plan updated based on correlation of measured scanner data with the property being measured according to the sample plan. In this embodiment, the approach is determination of a sampling plan using a known correlation between alignment data/leveling data and overlay/CDU (CD uniformity) data and to identify areas or wafers with better or worse correlation. Higher correlation would require less sampling.

The steps in this embodiment include:

1202—defining a sampling plan for measuring a property of a wafer.

1204—processing a wafer using the scanner.

1206—measuring processing data related to processing of the wafer using a scanner. The processing data may comprise alignment data and/or leveling data.

1208—measuring the property of a substrate; and

1210—determining the correlation of the processing data with the property 1212—updating the sampling plan based on the correlation of the processing data with the property. The updating of the sampling plan may include modifying the sampling across a wafer, for example by changing the sampling density and/or locations within the wafer, based for example upon the variation of the processing data.

1214—measuring the property of a wafer using the updated sampling plan.

Figure 13:
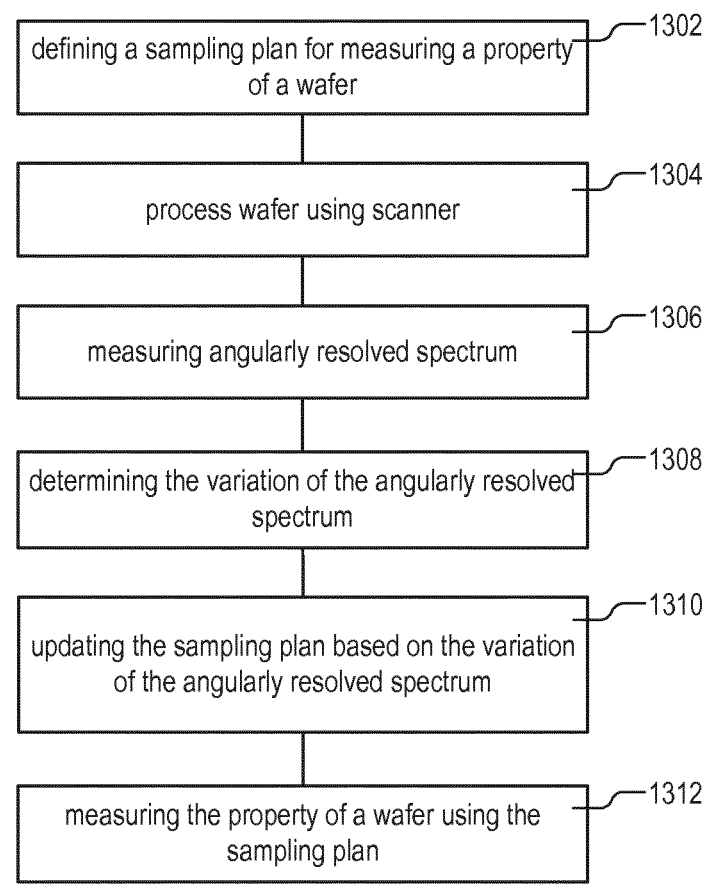
FIG. 13 is a flowchart illustrating an embodiment with the sampling plan updated based on variation of the angularly resolved spectrum of the metrology scatterometer.

FIG. 13 is a flowchart illustrating an embodiment with the sampling plan updated based on variation of the angularly resolved spectrum of the metrology scatterometer. The variation is a measure of the smoothness of the angular spectrum across the pupil plane of the scatterometer and the variation is sensitive to processing effects.

The steps are:

1302—defining a sampling plan for measuring a property of a wafer.

1304—processing a wafer using the scanner.

1306—measuring an angularly resolved spectrum of the wafer.

1308—determining the variation (for example standard deviation, sigma) of the angularly resolved spectrum. The variation may be estimated from a single measurement point.

1310—updating the sampling plan based on the variation of the angularly resolved spectrum. and

1312—measuring the property of a wafer using the updated sampling plan.

Figure 14:
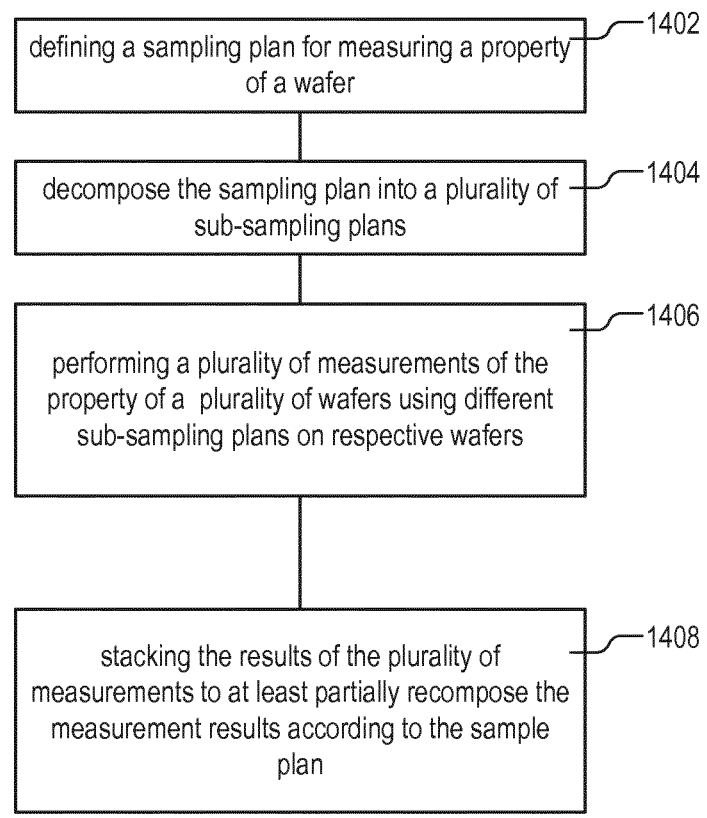
FIG. 14 is a flowchart illustrating an embodiment with the sampling plan decomposed into a plurality of sub-sampling plans.

FIG. 14 is a flowchart illustrating an embodiment with the sampling plan decomposed into a plurality of sub-sampling plans. By decomposing a dense sampling scheme and distributing over all the wafers in a lot, or multiple lots, processing drifts can be averaged, making the measurements more representative of the complete lot. Each wafer may be measured, enabling early flagging of wafers that suffer from large excursions. These wafers can be excluded from APC feedback loop updates and can be reworked instead of processed further. CPE corrections can be determined for each lot, allowing a faster and better feedback for CPE.

With reference to FIG. 14, the steps are:

1402—defining a sampling plan for measuring a property of a wafer.

1404—decompose the sampling plan into a plurality of sub-sampling plans. The sampling plan may be decomposed into a plurality of sub-sampling plans across a plurality of exposure fields of the wafers.

1406—performing a plurality of measurements of the property of a plurality of wafers using different sub-sampling plans on respective wafers.

1408—stacking the results of the plurality of measurements to at least partially recompose the measurement results according to the sample plan.

Figure 15A:
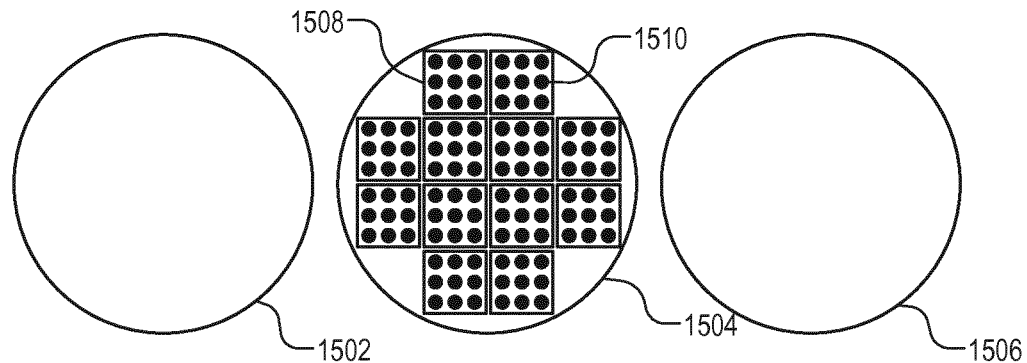
FIG. 15a illustrates a sampling plan for three wafers with complete sampling of one wafer.

FIG. 15a illustrates a sampling plan for three wafers with complete sampling of one wafer. With reference to FIG. 15a, a production lot has three wafers 1502-1506, of which only the second wafer 1504 is sampled. The squares 1508 are exposure fields, the dots 1510 are sample points in the sample plan and the large circles 1502-1504 represent the wafers. The approach of distributed sampling in accordance with an embodiment is to include the first and last wafers 1502 and 1506 (all wafers in this case) in the sampling plan, without increasing the total number of sampling points (12×9 in this example) per lot. That can be achieved in several ways, for instance using only the four center fields on all wafers as shown in FIG. 15b.

Figure 15B:
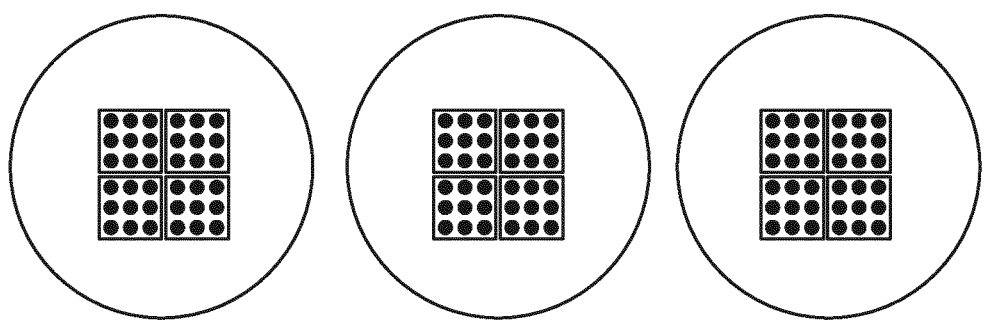
FIGS. 15b to 15c illustrate a sampling plan being decomposed across sub-sampling plans of three wafers.
Figure 15C:
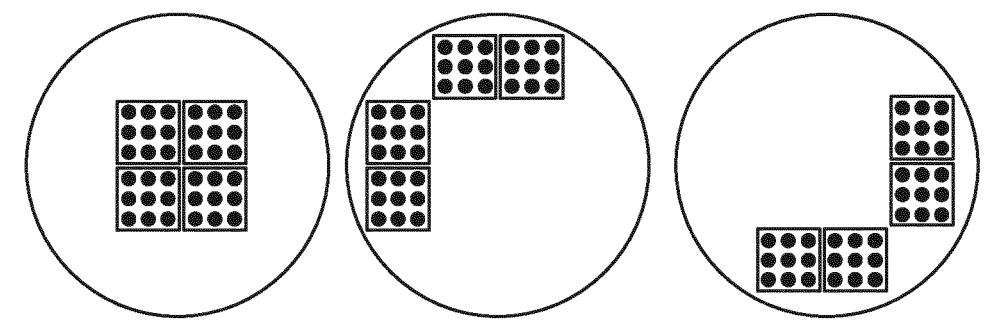

FIGS. 15b to 15c illustrate a sampling plan being decomposed across sub-sampling plans of three wafers. The example of FIG. 15b does however not give the original spatial distribution, if all three sample plans on wafer level are stacked together. This will result in a worse estimation of the properties of the sampled lot.

Another choice that does allow for correct stacking is illustrated in FIG. 15c. However, if the distribution is done carelessly, as is done in the example of FIG. 15c, the sampling results per wafer may yield unusable results again, because the estimation for some wafers may not be very accurate.

Figure 16A:
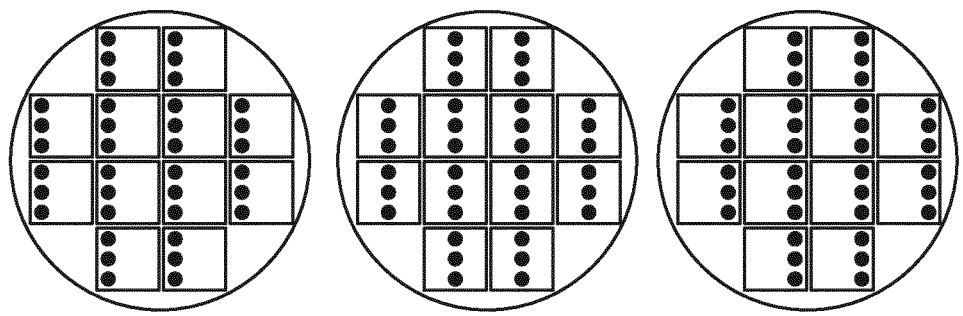
FIGS. 16a and 16b illustrate a sampling plan being decomposed across sub-sampling plans of three wafers in a better way than illustrated in FIGS. 15b and 15c.
Figure 16B:
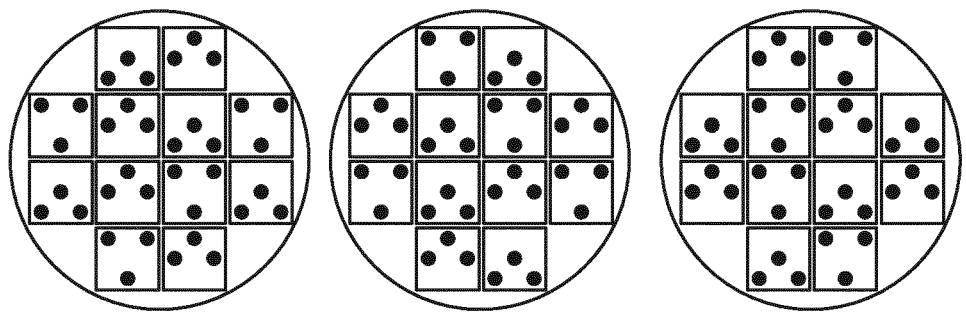

FIGS. 16a and 16b illustrate a sampling plan being decomposed across sub-sampling plans of three wafers in a better way than illustrated in FIGS. 15b and 15c. The sub-sample plans are optimized per wafer, such that (1) the decomposed sampling schemes are useful, and (2) they can be stacked together to the original layout. For instance the scheme illustrated in FIG. 16a has a better cross-wafer spatial distribution, compared to that of FIG. 15c. This scheme has similar problems however, but at the cross-field level, and the estimation of the properties of the fields cannot be determined reliably. If this finer detail is also taken into account, one may end up with an optimal scheme as illustrated in FIG. 16b.

Figure 16C:
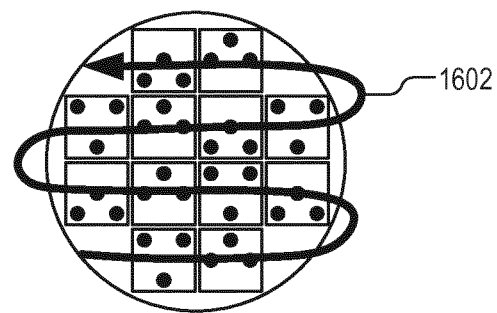
FIG. 16c illustrates the exposure order for fields and a sub-sampling plan.

FIG. 16c illustrates the exposure order for fields and a sub-sampling plan. The decomposition of the intrafield sampling plans is performed such that each three consecutive fields, in the exposure order illustrated by the serpentine line 1602 in FIG. 16c, stacked together result in a complete field.

The layouts illustrated in FIGS. 15c, 16a and 16b all are "complete", that is, when the sub-sampling plans of all wafers are stacked there are not "empty" spaces in the sample plan. Other embodiments may have the full sample plan (here 12 fields of 9 marks) less dense so as to cover only part of possible measurement sites on the wafer.

Figure 17:
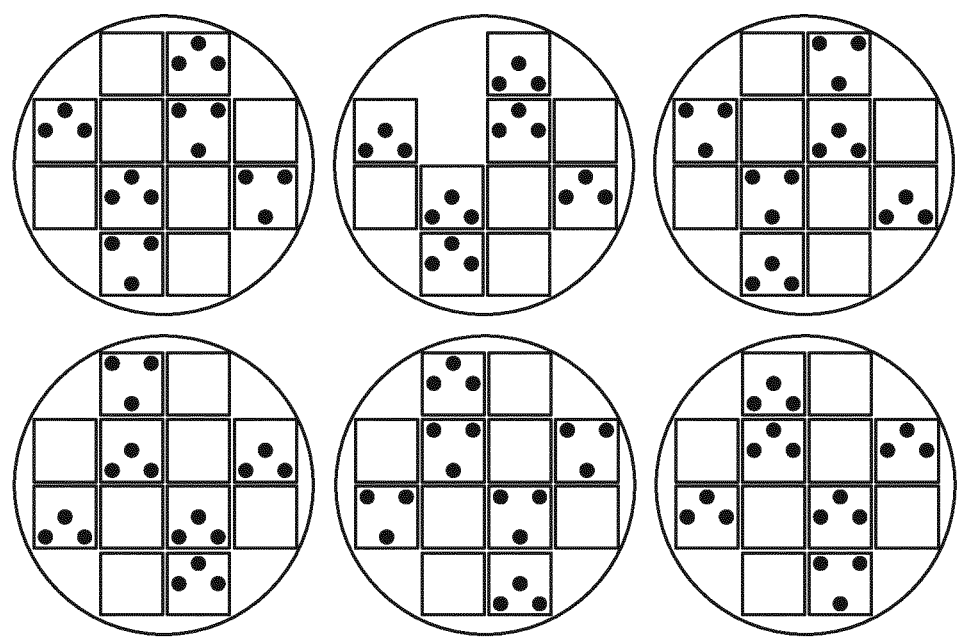
FIG. 17 illustrates a sampling plan being decomposed across sub-sampling plans of six wafers with some fields being not sampled.

Another embodiment has an "incomplete" decomposed sampling plan. FIG. 17 illustrates sampling plan being decomposed across sub-sampling plans of six wafers with some fields being not sampled. In this example, the lot size is six wafers instead of three, and the sample plan can be decomposed as shown in FIG. 17, where again the squares are exposure fields, the dots are sample points and the large circles represent the wafers. Some fields are skipped at some wafers, other fields are skipped at other wafers. When all sub-sampling plans are stacked together, the complete sample plan is achieved. This applies for all levels of granularity: not all fields need to be measured (as shown in FIG. 17), not all wafers need to be measured, and/or not all lots need to be measured.

Furthermore, if the number of wafers within one lot is not sufficient to allow this decomposition, multiple lots may be used. This would mean running two or more different static sampling plans in lot production.

Process control has been applied to the semiconductor industry for many years. Wafers are measured with metrology tools and a correction model is applied to measured data in order to calculate model parameters. Those parameters are then used to control the process. Therefore, the performance of process control depends on metrology measurement scheme and correction model. It is known that there is a trade-off between metrology measurement effort and modeling accuracy.

Several optimality statistical criteria are used to optimize a metrology sampling scheme based on a given correction model. A popular optimality criterion is normalized model uncertainty (also called as G-optimality). The inference of normalized model uncertainty is shown below.

Least-Square Estimation:

$$y = C\beta + \epsilon \Rightarrow \hat{\beta} = (C^T C)^{-1} C^T y$$

Assume y refers to measured data and $y \in R^{m \times 1}$, m represents the number of measured points of a reduced sampling scheme; C represents a design matrix of a reduced sampling scheme, and $C \in R^{m \times n}$, n refers to the number of fit coefficients, $\beta$ indicates correctable parameters and $\beta \in R^{n \times 1}$. $c_p$ refers to a design matrix of any measurable position P and $C_p \in R^{n \times 1}$. $\epsilon$ represents residual errors and $\epsilon \in R^{m \times 1}$.

By assuming $$\beta = \begin{bmatrix} \beta_0 \\ \bullet \\ \beta_k \end{bmatrix} \text{ and } C_p = \begin{bmatrix} 1 \\ \bullet \\ x_{kp} \end{bmatrix}$$

correctable errors at point P can be calculated as $$y_p = \beta_0 + \beta_1 x_{1p} + \ldots + \beta_k x_{kp}$$

$$y'_p - E(y_p) = \beta'_0 - \beta_0 + (\beta'_1 - \beta_1)x_{1p} + \ldots + (\beta'_k - \beta_k)x_{kp} = C_p^T(\beta' - \beta)$$

$$\sigma^2_{y'_p} = E[(y'_p - E(y_p))^2] = E[c_p^T(\beta' - \beta)(\beta' - \beta)^T c_p] \because y = C\beta + \varepsilon$$

$$= c_p^T E[(C^T C)^{-1} C^T \varepsilon \varepsilon^T C((C^T C)^{-1})^T] c_p$$

$$= \sigma^2_{noise} c_p^T (C^T C)^{-1} c_p$$

where $\sigma_{noise}^2 = [\varepsilon \varepsilon^T]$.

Therefore, $\sigma_{y'_p}$=definition of model uncertainty $$\sigma_{noise} \sqrt{c_p^T (C^T C)^{-1} c_p}$$

The definition of normalized model uncertainty $$= \sigma_{y'_p}/\sigma_{noise} = \sqrt{c_p^T (C^T C)^{-1} c_p}$$

As can be seen, the physical meaning of model uncertainty is standard deviation of correctable errors for given position. By using a reduced sampling scheme and correction model, a design matrix can be built. By assuming that the same variance at each position ($\sigma_{noise}^2 = E[\varepsilon \varepsilon^T]$, $\sigma_{noise}$ is a constant), normalized model uncertainty can be calculated per measurable (or specified) position. Following that, statistical measures, e.g. maximum, mean plus 3sigma ... etc, can be used to evaluate a reduced sampling scheme. The optimal sampling scheme can then be determined.

Figure 18:
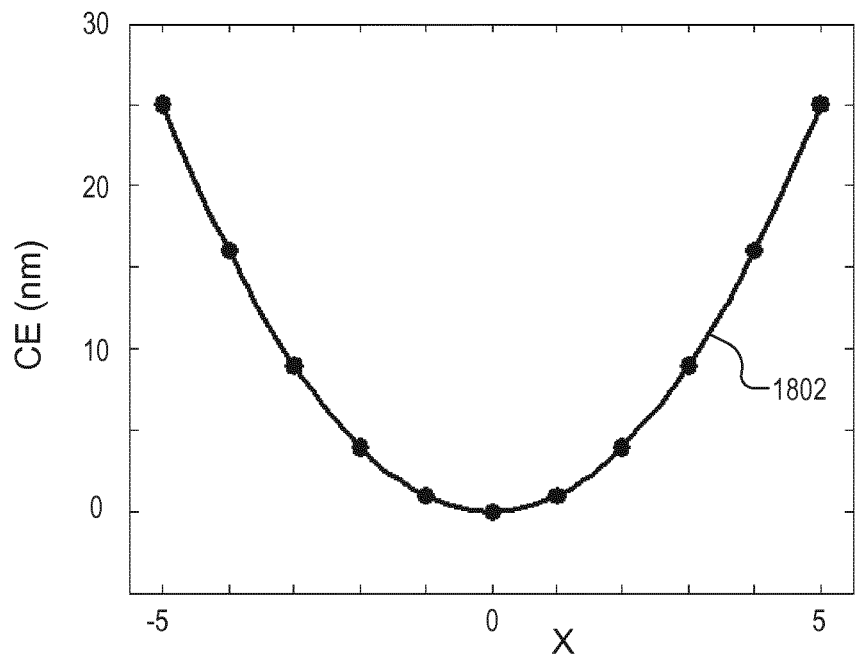
FIG. 18 is a graph of correctable errors versus position across a wafer.

A simple example is now given, with reference to FIG. 18, to explain the use of metrology sampling scheme optimization (SSO). FIG. 18 is a graph of correctable errors, CE, in nm, versus metrology position, X, across a wafer. The following are assumed:

(a) The full metrology layout is [−5, −4, −3, −2, −1, 0, 1, 2, 3, 4, 5], which is 11 positions in total, shown as black circles in FIG. 18.

(b) The fingerprint (or correctable errors) is shown in FIG. 18 as a parabolic fit curve 1802 and $y=\beta_0+\beta_1 x+\beta_2 x^2$, a given correction model.

(d) $\sigma_{noise}=1$ nm (uniform metrology measurement noise and process effect over a wafer).

(c) There are no non-correctable errors (so-called NCE or residual).

In this case, the fingerprint calculated by measuring any 5 positions has no difference from measuring full metrology layout with 11 positions. In fact, measuring at least more than 2 positions is sufficient and it doesn't matter at which positions the measurements are performed.

Figure 19:
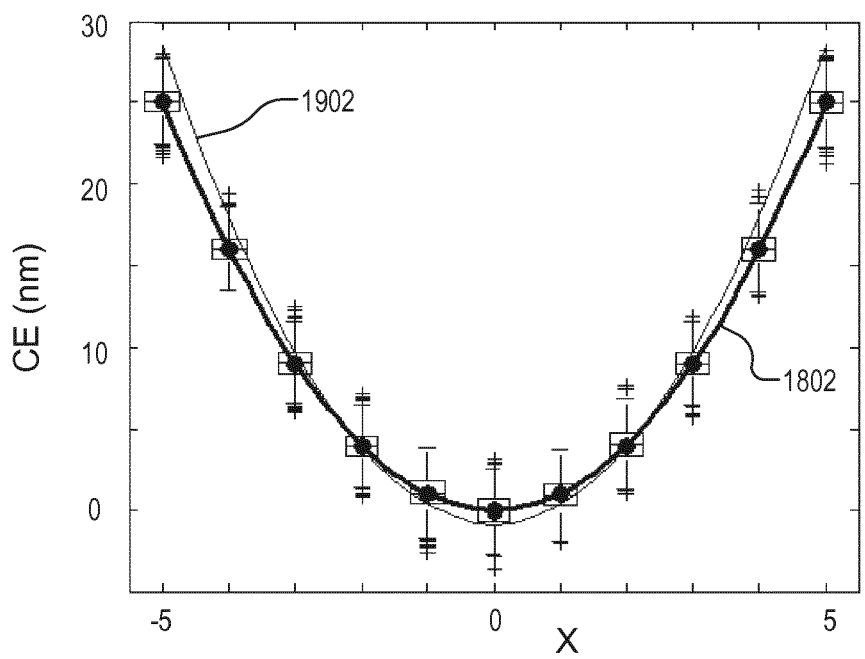
FIG. 19 is a graph of correctable errors versus position across a wafer, with metrology noise added.

With reference to FIG. 19, if real-world metrology noise (with an assumed normal distribution) is imposed to each position with 1 nm-sigma, the fit curve 1902, even calculated from full layout, could deviate from the baseline fit curve 1802. The fit curve delta between the curves 1802 and 1902 is actually the correctable delta. It can be exaggerated for a reduced sampling scheme. If [−1, 0, 1] were a reduced scheme, the fit curve could become upside-down, which would lead to significant large correctable delta.

Per position, normalized model uncertainty is equal to standard deviation of correctable delta. Hence, normalized model uncertainties for measuring full layout may be calculated as shown below.

In previous approaches using normalized model uncertainty (or G-optimality), it is assumed that every position has the same variances. However, in reality, the edge of a wafer suffers from more significant process effect than intermediate area of a wafer, and so does the center of a wafer (where photo resist is deposited) and there sometimes exists unknown localized effects. These result in position-dependent variances. Besides, the deformation of overlay targets is not consistent over a wafer either. So the metrology measurement noise shall be considered to be position-dependent as well.

Because of non-uniform process effect/metrology noise over a wafer, the assumption made in previous approaches is no longer valid. An output optimal sampling scheme will be less robust in the real world.

In accordance with an embodiment, weighted least square (WLS) estimation is used to take position-dependent variances into account. The equation of model uncertainty is then re-inferred as shown below:

$$\text{model uncertainty, } \sigma_{y'_p} = \sqrt{c_p^T (C^T W C)^{-1} c_p},$$

where $$W = \begin{bmatrix} 1/\sigma_1^2 & 0 & 0 \\ \ldots & \ldots & \ldots \\ 0 & 0 & 1/\sigma_k^2 \end{bmatrix}$$

where $\sigma_i^2$ represents the variance at position i of a reduced sampling scheme, k refers to the total number of measured positions of a reduced sampling scheme. This is referred to as weighted model uncertainty in order to differentiate from normalized model uncertainty.

By using a reduced sampling scheme and correction model, a design matrix can be built. By using a variance per sampling position, model uncertainty can be calculated. The same statistical measures may be used to evaluate the performance of a reduced sampling scheme. Hence, an optimal sampling scheme can be determined.

Figure 20:
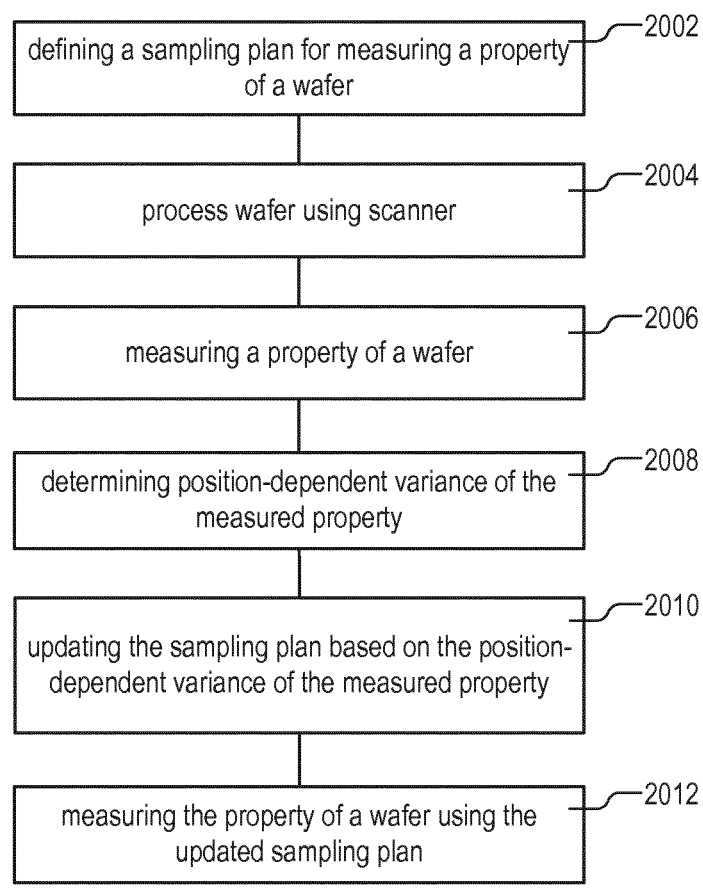
FIG. 20 is a flowchart illustrating an embodiment with the sampling plan updated based on position-dependent variation of the property being measured.

FIG. 20 is a flowchart illustrating an embodiment with the sampling plan updated based on position-dependent variation of the property being measured according to the sample plan.

The steps in this embodiment include:

2002—defining a sampling plan for measuring a property of a wafer.

2004—processing a wafer using the scanner;

2006—measuring the property of a substrate;

2008—determining the position-dependent variance the property and

2010—updating the sampling plan based on the position-dependent variance of the measured property. The updating of the sampling plan may include modifying the sampling across a wafer, for example by changing the sampling density and/or locations within the wafer, based for example upon the position-dependent variance of the measured property and using, for example, weighted least-square (WLS) estimation.

2012—measuring the property of a wafer using the updated sampling plan.

FIGS. 21 to 24 illustrate the effect of using weighted model uncertainty rather than normalized model uncertainty with various simulated position dependent variances.

Figure 21:
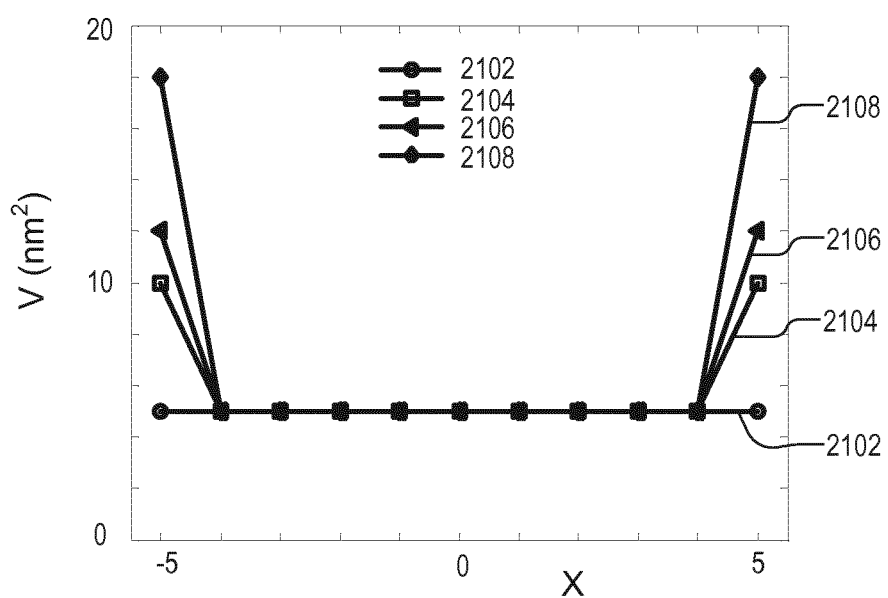
FIG. 21 is a graph of four types of simulated noise versus position across a wafer.

Four different noise types are simulated and shown in FIG. 21. The wafer edge variance is gradually increased from type to type.

Based on noise type 2102, which is not position-dependent, the optimal sampling scheme is at X positions across the wafer [−5, 0, 5]. This scheme can be applied to use cases with different variances at the edge, corresponding to noise types 2104, 2106 and 2108 illustrated in FIG. 20. These use cases are illustrated in FIGS. 22 to 24 in which bigger markers refer to optimal sampling positions.

Figure 22:
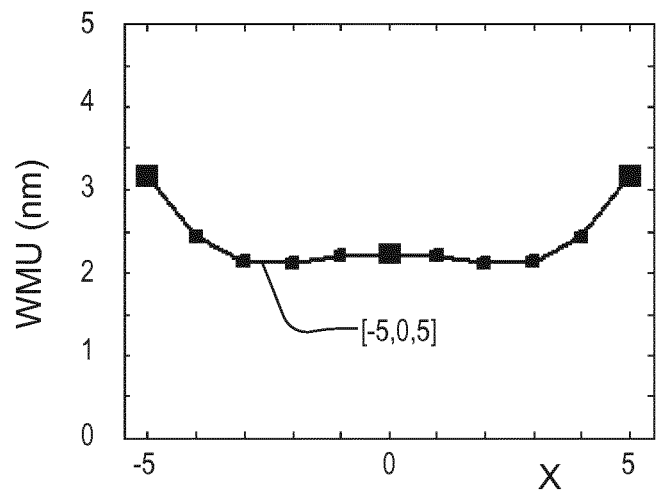
FIG. 22 is a graph of calculated weighted model uncertainty for a noise type with 10 nm wafer edge variance.

FIG. 22 is a graph of the weighted model uncertainty, in nm, for the noise type with 10 nm wafer edge variance, corresponding to 2104 in FIG. 21. As can be see in FIG. 22, when edge variance has been increased from 5 nm to 10 nm, the optimal scheme still stands as [−5, 0, 5].

Figure 23:
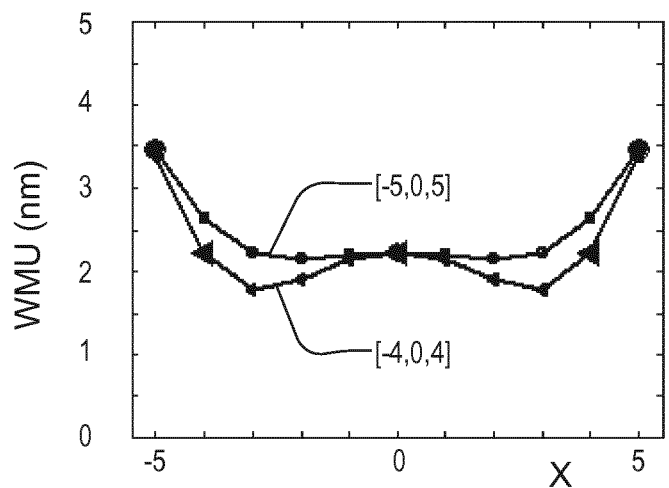
FIG. 23 is a graph of calculated weighted model uncertainty for a noise type with 12 nm wafer edge variance.

Once the edge variance is boosted to 12 nm, corresponding to 2106 in FIG. 21, as illustrated in FIG. 23, the sampling scheme [−4, 0, 4] starts to perform better than [−5, 0, 5].

Figure 24:
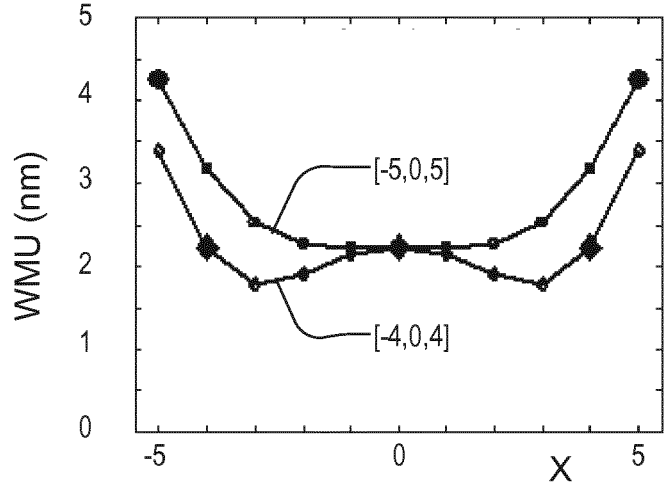
FIG. 24 is a graph of calculated weighted model uncertainty for a noise type with 10 nm wafer edge variance.

The difference can be even increased to ~1 nm if the edge variance reaches 18 nm, corresponding to 2108 in FIG. 21, as illustrated in FIG. 24. Thus it can be seen that an optimal scheme may obtained using position-dependent variances instead of uniform variances.

The embodiment described with reference to FIGS. 14 to 17 provides an example of operation of a method that can be implemented with an inspection apparatus. For example, with reference to FIGS. 4 and 25, an inspection apparatus may be configured for measuring a property of a plurality of substrates, the inspection apparatus comprising:
- an illumination system, 2, 12, 13, 15, 16, 17 in FIG. 4, configured to illuminate a substrate with radiation;
- a detection system, 18 and PU in FIG. 4, configured to detect scattered radiation arising from the illumination; and
- at least one processor, for example PU in FIG. 4, configured, now with reference to FIG. 25, to:

2506—produce a sampling plan defined for measuring a property of a substrate, wherein the sampling plan comprises a plurality of sub-sampling plans. The sampling plan may be constrained to a predetermined fixed number of measurement points;

2508—control the inspection apparatus to perform a plurality of measurements of the property of a plurality of substrates using different sub-sampling plans for respective substrates; and 2510—optionally, stack the results of the plurality of measurements to at least partially recompose the measurement results according to the sample plan.

The embodiment described with reference to reference to FIGS. 14 to 17 may be combined, for example, with features of the embodiment described with reference to FIG. 11.

Such an example may be implemented in an inspection apparatus, such as may be described with reference to FIGS. 4 and 26. The at least one processor, for example PU in FIG. 4, may be configured, with reference to FIG. 26, to:

2602—receive measured processing data related to processing of at least one substrate using a processing apparatus;

2604—determine variation of the processing data; and

2606—produce the sampling plan based on the variation of the processing data.

Figure 25:
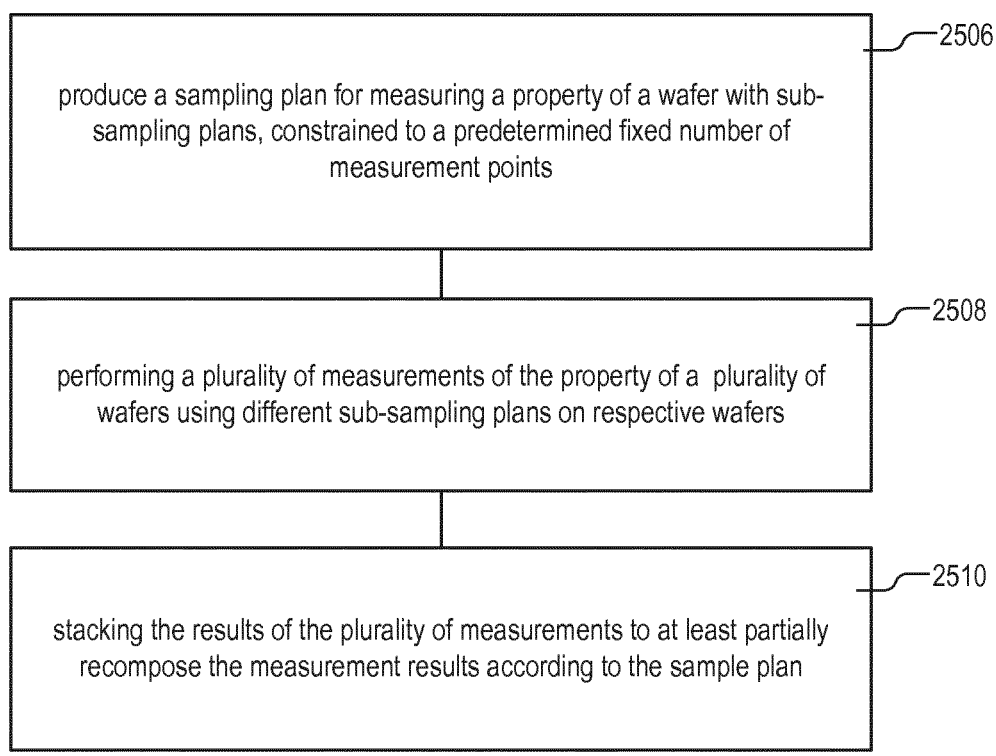
FIG. 25 is a flowchart illustrating an embodiment producing a sampling plan with sub-sampling plans that are used on respective wafers.
Figure 26:
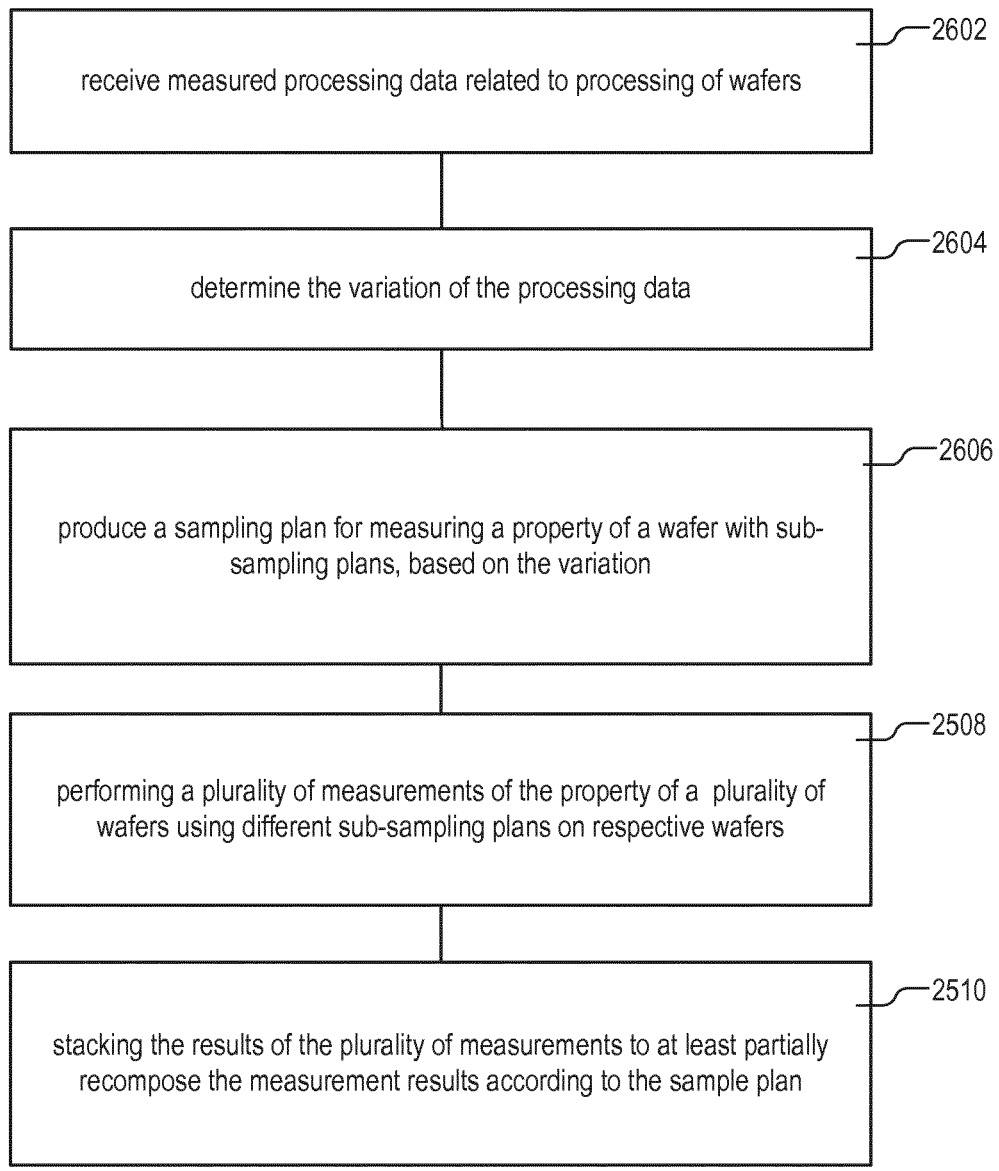
FIG. 26 is a flowchart illustrating an embodiment with a sampling plan with sub-sampling plans being produced based on variation of processing data.

The steps 2508 and 2510 in FIG. 26 are the same as described with reference to FIG. 25.

The embodiment described with reference to reference to FIGS. 14 to 17 may also be combined, for example, with features of the embodiment described with reference to FIG. 12.

Such an example may be implemented in an inspection apparatus, such as may be described with reference to FIGS. 4 and 27. The at least one processor, for example PU in FIG. 4, may be configured, with reference to FIG. 27, to:

2702—receive measured processing data related to processing of at least one substrate using a processing apparatus, such as alignment data or levelling data and receive measurements of a property of at least one substrate;

2704—determine a correlation of the measured processing data with the measurements of the property; and 2706—produce the sampling plan based on the correlation of the processing data with the measured property.

Figure 27:
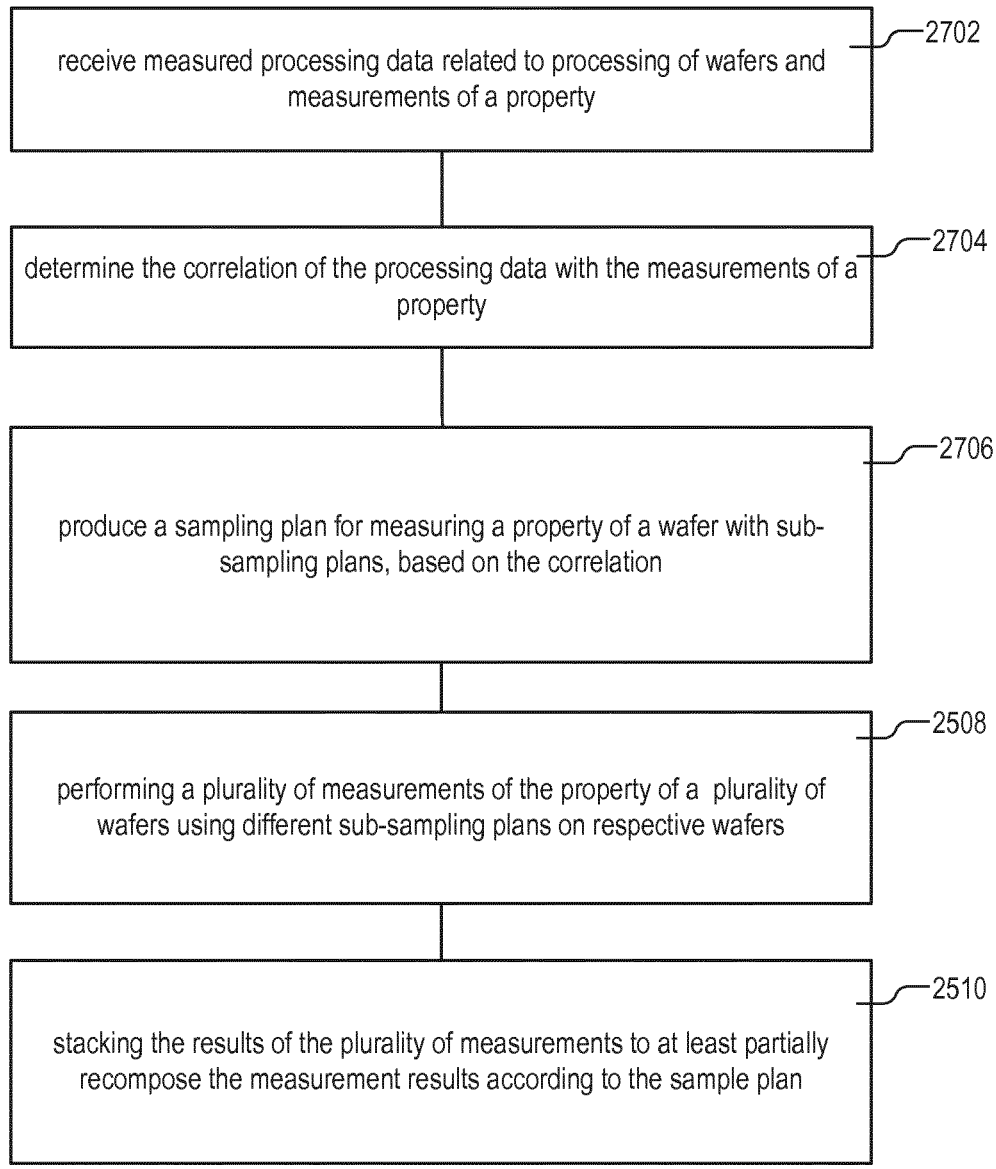
FIG. 27 is a flowchart illustrating an embodiment with a sampling plan with sub-sampling plans being produced based on correlation of processing data with the property being measured.

The steps 2508 and 2510 in FIG. 27 are the same as described with reference to FIG. 25.

The embodiment described with reference to reference to FIGS. 14 to 17 may also be combined, for example, with features of the embodiment described with reference to FIGS. 9 and 20.

Such an example may be implemented in an inspection apparatus, such as may be described with reference to FIGS. 4 and 28. The at least one processor, for example PU in FIG. 4, may be configured, with reference to FIG. 28, to:

2802—receive information on a characteristic affecting the substrates differently in two or more coordinates across a substrate. The information may comprise process setup information, such as scanner process job information and/or scanner actuator information. The information may comprise position-dependent variance across a substrate of the measured property; and 2806—produce the sampling plan configured to be different in two or more coordinates across the substrate based on the received information on the characteristic. When the information comprises position-dependent variance across a substrate of the measured property, the at least one processor may be configured to produce the sampling plan using weighted least-squares estimation, as described with reference to FIG. 20.

Figure 28:
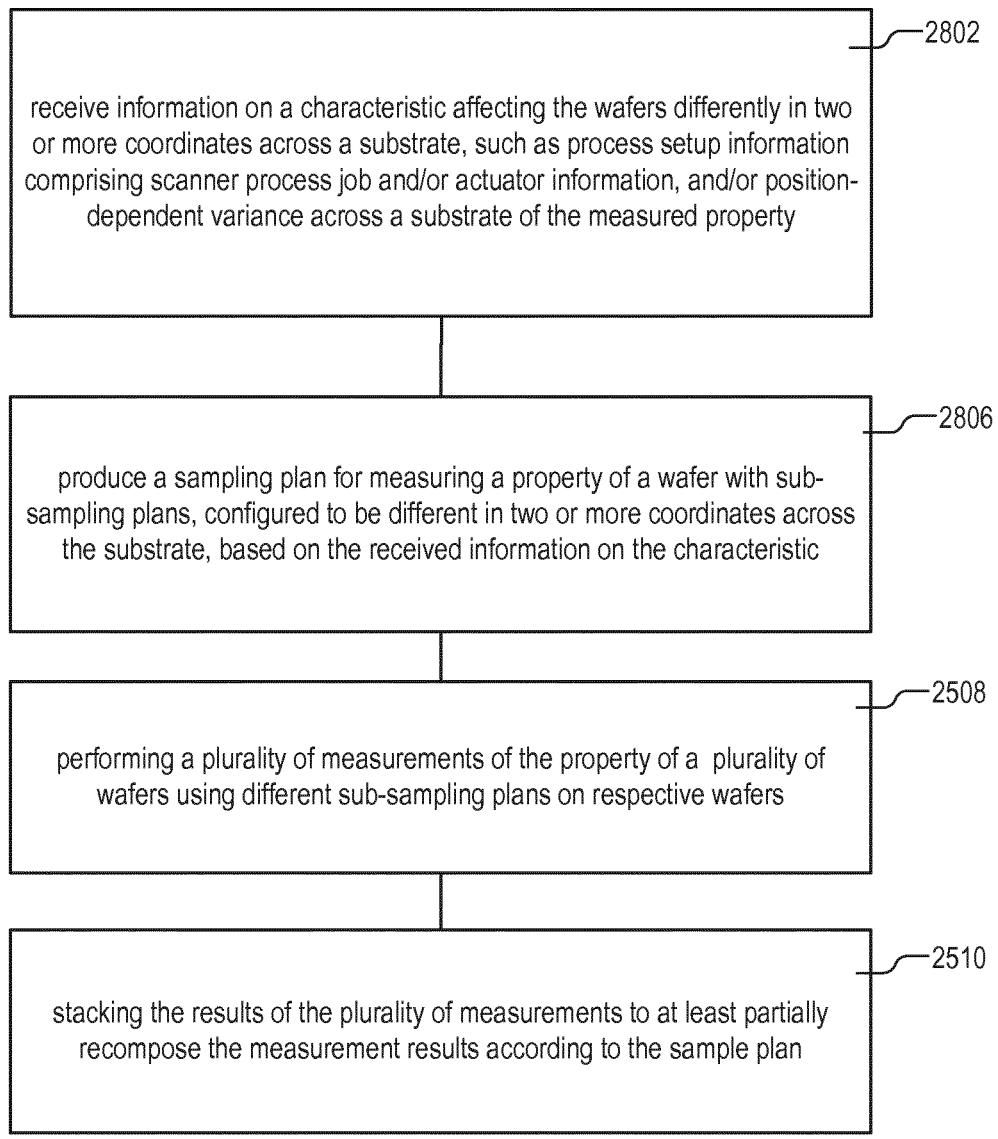
FIG. 28 is a flowchart illustrating an embodiment with a sampling plan with sub-sampling plans being configured to be different in two or more coordinates across a wafer.

The steps 2508 and 2510 in FIG. 28 are the same as described with reference to FIG. 25.

The embodiment described with reference to reference to FIGS. 14 to 17 may also be combined, for example, with features of the embodiment described with reference to FIGS. 9 and 20, including the updating of the sample plan.

Such an example may be implemented in an inspection apparatus, such as may be described with reference to FIGS. 4 and 29. The at least one processor, for example PU in FIG. 4, may be configured, with reference to FIG. 29, to:

2900—control the inspection apparatus to perform a plurality of measurements of the property of a plurality of substrates using different sub-sampling plans for respective substrates. This may be after production of the sampling plan, in accordance with steps 2506 and 2508 in FIG. 25.

2802—as described with reference to 2802 in FIG. 28, receive information on a characteristic affecting the substrates differently in two or more coordinates across a substrate. The information may comprise process setup information, such as scanner process job information and/or scanner actuator information. The information may comprise position-dependent variance across a substrate of the measured property;

2906—produce the sampling plan updated separately in two or more coordinates across the substrate based on the received information on a characteristic affecting the substrates differently in two or more coordinates across a substrate. When the information comprises position-dependent variance across a substrate of the measured property, the at least one processor may be configured to produce the sampling plan using weighted least-squares estimation, as described with reference to FIG. 20; and

2908—control the inspection apparatus to perform a plurality of measurements of the property of at least one substrate using different updated sub-sampling plans for the respective at least one substrate.

Figure 29:
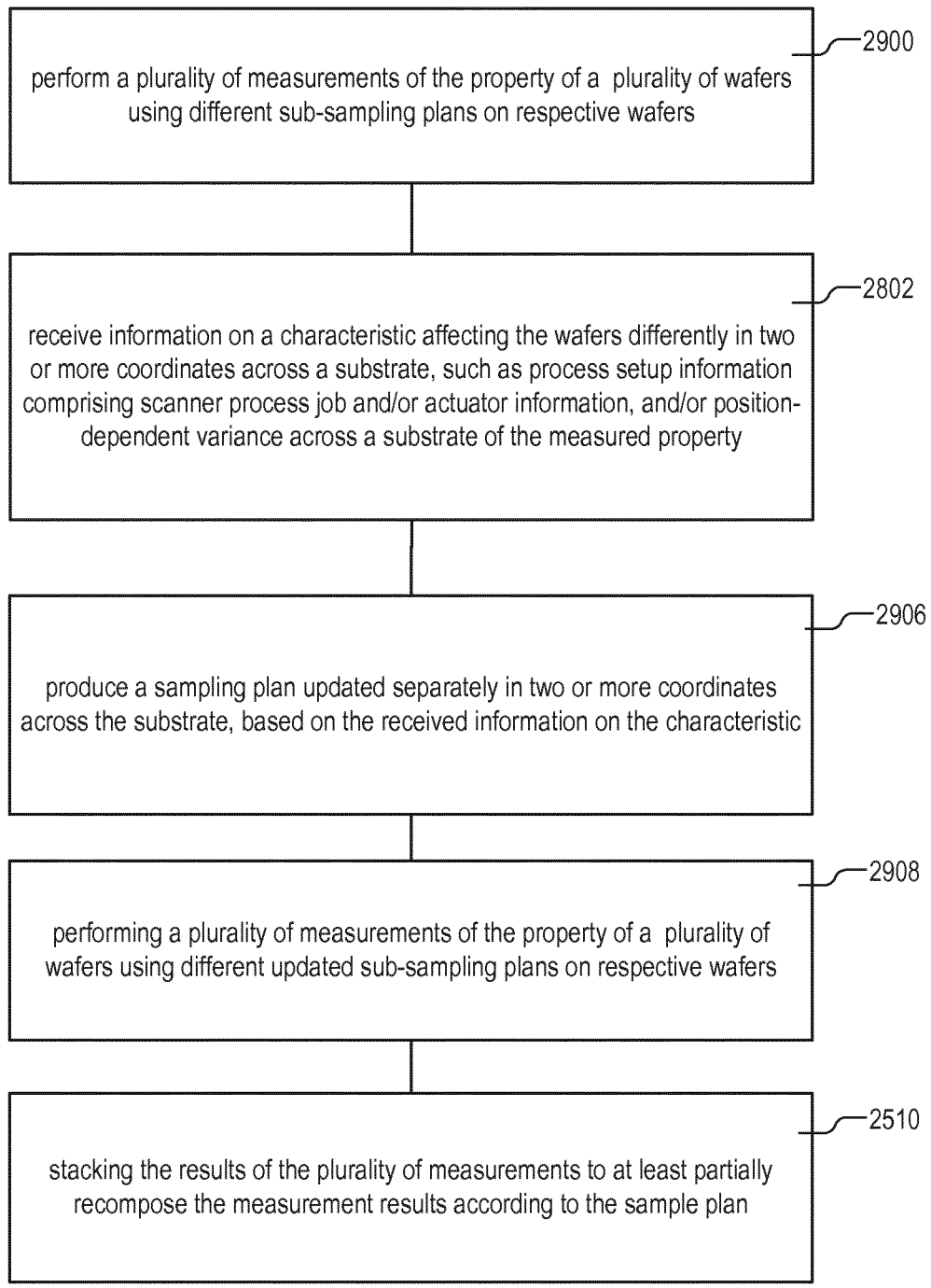
FIG. 29 is a flowchart illustrating an embodiment with a sampling plan with sub-sampling plans being updated separately in two or more coordinates across a wafer.

The step 2510 in FIG. 29 is the same as described with reference to FIG. 25.

It is possible to separate between within wafer and wafer-to-wafer measurements by distributing the sampling plan across more than one wafer using the sub-sampling plans and thus define two categories of measurement points. The first category is for "within wafer" information and the second category is for "between wafer" information. Furthermore, as has been described, sampling may be varied in two or more coordinates (for example x, y and/or radius). Both approaches achieve an optimally controlled lithographic apparatus on the basis of a given constraint of a maximum number of say M measurements over a series of N exposed and measured wafers. The optimal control may be quantified using the standard deviation of error of a property such as overlay or alignment.

The distribution can thus involve selection of a number of measurement points per wafer over a plurality of wafers and also the determination of the location of the measurement points across the wafer.

For the distribution over a plurality of wafers: a number selection can be made: n1 measurement points for the within wafer information and n2 measurement points for between wafer information; next a location distribution for both n1 and n2 may be made (where n1+n2 is about M/N). For this sampling optimization the quality of the model (expressed in model uncertainty and non-correctable residuals) may be used as a boundary condition.

For the distribution across the wafer, a location distribution may be used which in density is different in x, y and/or radius to match for differences in these directions with respect to, for example: lithography or metrology equipment capabilities; chip design rules with different constraints in x versus y direction; and wafer process effects with radial or irregular variation patterns. These differences may be used as pre-information/boundary conditions for sampling optimization.

Embodiments can be used on a stand-alone metrology tool, but running on an integrated tool is also convenient because the cluster throughput of a scanner with an integrated metrology tool may be used optimally.

The methods described herein can be implemented using the processing unit PU of an inspection apparatus. The processing unit can be integrated in the scatterometer, as illustrated in FIGS. 3 and 4, or it may be located elsewhere, for example as a stand-alone unit, or distributed across apparatuses which may include the inspection apparatus.

Embodiments also include computer program products containing one or more sequences of machine-readable instructions for measuring a property of a substrate, the instructions being adapted to cause one or more processors to perform a method or steps according to any of the embodiments described herein.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments in the context of optical lithography, it will be appreciated that embodiments may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 365, 355, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments have been described above, it will be appreciated that the invention may be practiced otherwise than as described. For example, the invention may take the form of a computer program containing one or more sequences of machine-readable instructions describing a method as disclosed above, or a data storage medium (e.g. semiconductor memory, magnetic or optical disk) having such a computer program stored therein.

The descriptions above are intended to be illustrative, not limiting. Thus, it will be apparent to one skilled in the art that modifications may be made to the invention as described without departing from the scope of the claims set out below.

The invention claimed is:

1. An inspection apparatus comprising:
 a detector configured to detect scattered radiation arising from a substrate illuminated with radiation; and
 at least one processor configured to:
  produce a sampling plan defined for measuring a property of a substrate, wherein the sampling plan comprises a plurality of sub-sampling plans; and
  control the inspection apparatus to perform a plurality of measurements of the property of a plurality of substrates using different one of the plurality of sub-sampling plans for respective ones of the substrates.

2. The inspection apparatus of claim 1, wherein the at least one processor is configured to produce the sampling plan constrained to a predetermined fixed number of measurement points.

3. The inspection apparatus of claim 1, wherein the at least one processor is configured to produce the sampling plan that is configured to be distributed across a plurality of exposure fields of the plurality of substrates.

4. The inspection apparatus of claim 1 wherein t e at least one processor is further configured to:
receive measured processing data related to processing of at least one substrate using a processing apparatus;
determine variation of the processing data; and
produce the sampling plan based on the variation of the processing data.

5. The inspection apparatus of claim 1, wherein the at least one processor is further configured to:
receive measured processing data related to processing of at least one substrate;
receive measurements of a property of at least one substrate;
determine a correlation of the measured processing data with the measurements f the property; and
produce the sampling plan based on the correlation of the processing data with the measured property.

6. The inspection apparatus of claim 5, wherein the processing data comprises alignment data.

7. The inspection apparatus of claim 5, wherein the processing data comprises leveling data.

8. The inspection apparatus of claim 1, wherein the at least one processor is further configured to:
receive information on a characteristic affecting the substrates differently in two or more coordinates across a substrate; and
produce the sampling plan configured to be different in two or more coordinates across the substrate based on the received information on the characteristic.

9. The inspection apparatus of claim 8, wherein the at least one processor is further configured to:
produce the sampling plan updated separately in two or more coordinates across the substrate based on the received information on a characteristic affecting the substrates differently in two or more coordinates across a substrate; and
control the inspection apparatus to perform a plurality of measurements of the property of at least one substrate using different updated sub-sampling plans for the respective at least one substrate.

10. The inspection apparatus of claim 8, wherein the information on a characteristic affecting the substrates differently in two or more coordinates across a substrate comprises process setup information.

11. The inspection apparatus of claim 10, wherein the process setup information comprises scanner process job information.

12. The inspection apparatus of claim 10, wherein the process setup information comprises scanner actuator information.

13. The inspection apparatus of claim 8, wherein the information on a characteristic affecting the substrates differently in two or more coordinates across a substrate comprises position-dependent variance across a substrate of the measured property.

14. The inspection apparatus of claim 13, wherein the at least one processor is configured to produce the sampling plan using weighted least-squares estimation.

15. A lithography apparatus comprising:
an exposure system comprising:
an illuminator configured to condition a radiation beam;
a support structure configured to support a patterning device;
a substrate table configured to support a substrate;
a projection system configured to project a pattern imparted to the radiation beam by the patterning device onto the substrate; and
an inspection apparatus comprising:
a detector configured to detect scattered radiation arising from the substrate illuminated with radiation; and
at least one processor configured to:
produce a sampling plan defined for measuring a property of a substrate, wherein the sampling plan comprises a plurality of sub-sampling plans; and
control the inspection apparatus to perform a plurality of measurements of the property of a plurality of substrates using a different one of the plurality of sub-sampling plans for respective ones of the substrates;
control the exposure system to expose the plurality of substrates prior to controlling the inspection apparatus to perform the plurality of measurements of the property of the plurality of substrates; and
control the exposure system to process a subsequent at least one substrate with conditions based on the plurality of measurements.

16. A non-transitory computer program prod containing one or more sequences of machine-readable instructions for measuring a property of a substrate, the instructions being adapted to cause at least one processor to perform operations comprising:
illuminating a substrate with radiation;
detecting scattered radiation arising from illuminated substrate; and
producing a sampling plan defined for measuring a property of a substrate, wherein the sampling plan comprises a plurality of sub-sampling plans; and
performing a plurality of measurements of the property of a plurality of substrates using different one of the plurality of sub-sampling plans for respective ones of the substrates.

* * * * *